US008114440B2

(12) United States Patent
Murthy

(10) Patent No.: US 8,114,440 B2
(45) Date of Patent: Feb. 14, 2012

(54) PHARMACEUTICAL COMPOSITIONS FOR THE ADMINISTRATION OF APTAMERS

(75) Inventor: Yerramilli V. S. N. Murthy, Apex, NC (US)

(73) Assignee: Idexx Laboratories Inc., Westbrook, ME (US)

( * ) Notice: Subject to any disclaimer, the term of this patent is extended or adjusted under 35 U.S.C. 154(b) by 804 days.

(21) Appl. No.: 11/400,384

(22) Filed: Apr. 10, 2006

(65) Prior Publication Data

US 2007/0110827 A1 May 17, 2007

Related U.S. Application Data

(60) Provisional application No. 60/736,862, filed on Nov. 16, 2005.

(51) Int. Cl.
*A01N 37/18* (2006.01)
*A01N 37/02* (2006.01)
*A01N 43/38* (2006.01)
*A01N 43/50* (2006.01)
*A01N 57/26* (2006.01)
*A61K 31/16* (2006.01)
*A61K 31/22* (2006.01)
*A61K 31/40* (2006.01)
*A61K 31/415* (2006.01)
*A61K 31/685* (2006.01)

(52) U.S. Cl. .......... 424/641; 514/78; 514/400; 514/419; 514/550; 514/626

(58) Field of Classification Search .................. 424/641; 514/78, 400, 419, 550, 626
See application file for complete search history.

(56) References Cited

U.S. PATENT DOCUMENTS

| | | | |
|---|---|---|---|
| 5,270,163 A | 12/1993 | Gold et al. | |
| 5,332,834 A | 7/1994 | Bhattacharya et al. | |
| 5,459,127 A | 10/1995 | Felgner et al. | |
| 5,475,096 A | 12/1995 | Gold et al. | |
| 5,574,020 A | 11/1996 | Klink et al. | |
| 5,599,969 A | 2/1997 | Hardy et al. | |
| 5,629,020 A | 5/1997 | Leone-Bay et al. | |
| 5,788,983 A | 8/1998 | Chien et al. | |
| 5,877,212 A | 3/1999 | Yu et al. | |
| 6,887,487 B2 | 5/2005 | Murthy et al. | |
| 6,946,137 B2 | 9/2005 | Murthy et al. | |
| 2003/0165434 A1 | 9/2003 | Reinhard et al. | |
| 2003/0170289 A1* | 9/2003 | Chen et al. ............. | 424/426 |
| 2004/0171571 A1* | 9/2004 | Krieg et al. ............. | 514/44 |
| 2004/0197408 A1 | 10/2004 | Gravett | |
| 2004/0220264 A1 | 11/2004 | Yu et al. | |
| 2005/0124565 A1 | 6/2005 | Diener et al. | |
| 2005/0175708 A1 | 8/2005 | Carrasquillo et al. | |
| 2005/0192348 A1 | 9/2005 | Bar-Or et al. | |
| 2006/0122144 A1 | 6/2006 | Kane et al. | |
| 2006/0141054 A1* | 6/2006 | Piccariello ............. | 424/498 |
| 2006/0167088 A1* | 7/2006 | Widder et al. ............. | 514/513 |
| 2007/0111969 A1 | 5/2007 | Murthy | |

FOREIGN PATENT DOCUMENTS

| | | |
|---|---|---|
| WO | WO 2004/089239 | 10/2004 |
| WO | WO 2005/000241 | 1/2005 |
| WO | WO 2005/051174 | 6/2005 |

OTHER PUBLICATIONS

Griffin, et al., *The Discovery and Characterization of a Novel Nucleotide-Based Thrombin*, Gene, 137 (1993), pp. 25-31.
Jenison, et al., *Oligonucleotide Inhibitors of P-Selection-Dependent Neutrophil-Platelet Adhesion*, Antisense & Nucleic Acid Drug Development, vol. 8, (4): 265-279 (1998).
Bell, et al., *Oligonucleotide NX1838 Inhibits VEGF $_{165}$—Mediated Cellular Responses In Vitro*, In Vitro Cellular & Developmental Biology, Journal of the Society for In Vitro Biology, vol., 35 (9), pp. 533-542 (1999).
Watson, et al., *Anti-L-Selectin Aptamers: Binding Characteristics, Pharmacokinetic Parameters, and Activity Against an Intravascular Target In Vivo*, Antisense & Nucleic Acid Drug Development, 10:63-75 (2000), p. 63.
Daniels, et al., *Generation of RNA Aptamers to the G-Protein-Coupled Receptor for Neurotensin, NTS-1*, Analytical Biochemistry 305, pp. 214-226 (2002).
Chen, et al., *Inhibition of Heregulin Signaling by an Aptamer that Preferably Binds to the Oligomeric Form of Human Epidermal Growth Factor Receptor-3*, Proc. Natl. Acad. Sci. U.S.A. 100(16), pp. 9226-9231, PNAS, Aug. 5, 2003.
Khati, et al., *Neutralization of Infectivity of Diverse R5 Clinical Isolates of Human Immunodeficiency Virus Type 1 by gp120-Binding 2'F-RNA Aptamers*, Journal of Virology, Dec. 2003, pp. 12692-12698.
Vaish, et al., *A Novel, Modification-Dependent ATP-Binding Aptamer Selected from an RNA Library Incorporating a Cationic Functionality*, Biochemistry, 2003, 42, pp. 8842-8851.
Ellington, et al., *In Vitro Selection of RNA Molecules that Bind Specific Ligands*, Nature, vol. 346, Aug. 30, 1990, pp. 818-822.
Turek, et al., *Systematic Evolution of Ligands by Exponential Enrirchment: RNA Ligands to Bacteriophage T4 DNA Polymerase*, Aug. 3, 1990, Science, vol. 249, pp. 505-510.
Wlotzka, et al., In Vivo *Properties of an Anti GnRH Spiegelmer: An example of an Oligonucleotide-Based Therapeutic Substance Class*, (2002) Proc. Natl. Acad. Sci. U.S.A. 99 (13): pp. 8898-8902.
Reyderman, et al. (1998), *Pharmacokinetics and Biodistribution of a Nucleotide-Based Thrombin Inhibitor in Rats*, Pharmaceutical Research, vol. 15, No. 6, 1998, pp. 904-910.
Tucker, et al., *Detection and Plasma Pharmacokinetics of an Anti-Vascular Endothelian Growth Factor Oligonucleotide-Aptamer (NX1838) in Rhesus Monkeys*, Journal of Chromatography B, 732 (1999), pp. 203-212.

(Continued)

Primary Examiner — Johann Richter
Assistant Examiner — Luke Karpinski
(74) *Attorney, Agent, or Firm* — Haynes and Boone, LLP

(57) ABSTRACT

Pharmaceutical compositions comprising an aptamer and an amino acid ester or amide or an aptamer; a divalent metal cation; and a carboxylic acid, a phospholipid, a phosphatidyl choline, or a sphingomyelin. Methods of treating or preventing a condition in an animal comprising administering to the animal the pharmaceutical compositions.

29 Claims, 4 Drawing Sheets

OTHER PUBLICATIONS

Figure 1:
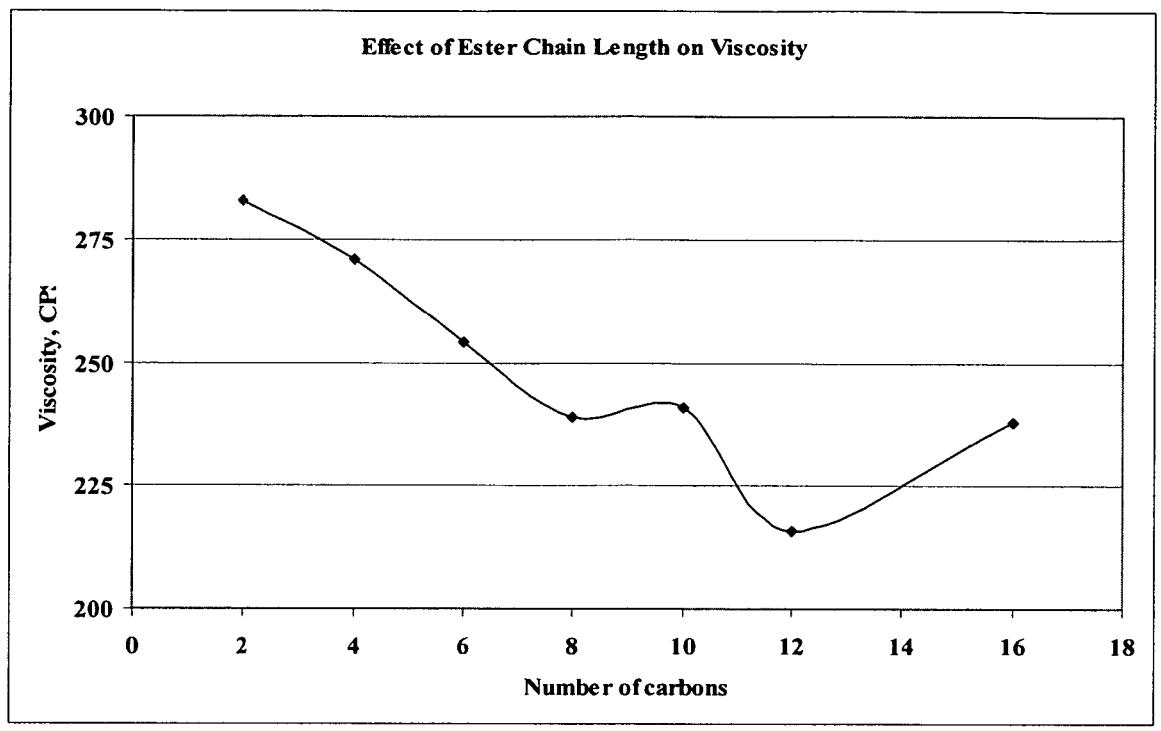

Green, et al., *Nuclease-Resistant Nucleic Acid Ligands to Vascular Permeability Factor/Vascular Endothelial Growth Factor*, Chem.& Biol. 2(10), pp. 683-695, 1995.

Jellinek, et al., *Potent 2'-Amino -2'-Deoxypyrimidine RNA Inhibitors of Basic Fibroblast Growth Factor*, Biochemistry 1995, 34, pp. 11363-11372.

Ruckman, et al., *2'-Fluoropyrimidine RNA-Based Aptamers to the 165-Amino Acid Form of Vascular Endothelial Growth Factor ($VEGH_{1165}$)*, The Journal of Biological Chemistry, vol. 273, No, 32, Issue of Aug. 7, 1998, pp. 20556-20567.

Uhlmann, et al., *Use of Minimally Modified Antisense Oligonucleotides for Specific Inhibition of Gene Expression*, in Methods in Enzymology, Antisense Technology, Part A, General Methods, Methods of Delivery, and RNA Studies, vol. 313, edited by M. Ian Phillips, Academic Press, San Diego., pp. 268-284, (2000).

Burmeister, et al., *Direct in Vitro Selection of a 2'-O-Methyl Aptamer to VEGF*, Chemistry and Biology, vol. 12, pp. 25-33, Jan. 2005.

International Search Report for PCT/US05/34415 dated Apr. 4, 2006.

Search Report and Written Opinion for PCT/US08/69951 dated Dec. 4, 2008.

Remington's Pharmaceutical Sciences, 16th ed., edited by A. Osol, Mack Publishing Company (1980), pp. 669-671.

H. Mok et al., PEG Assisted DNA Solubilization in Organic Solvents for Preparing Cytosol Specifically Degradable PEG/DNA Nanogels, Bioconjugate Chemistry, Nov./Dec. 2006, vol. 17, No. 6, p. 1369.

E. Brody et al., Aptamers as Therapeutic and Diagnostic Agents, Reviews in Molecular Biology, 74 (2000), 5-13.

J. F. Lee et al., Aptamer Therapeutics Advance, Current Opinions in Chemical Biology, 2006, 10:282-289.

R. R. White et al., Developing Aptamers Into Therapeutics, J. Clin. Invest., Oct. 2000, vol. 106, No. 8, pp. 929-934.

Hjalmarsson et al., *Aptamers Future toold for diagnostics and therapy*, Swedish Defense Research Agency, Apr. 2004.

K. Gephardt et al., *RNA Aptamers to S-Adenosylhomocysteine: Kinetic Properties, Divalent Cation Dependency, and Comparison with Anti-S-Adenosylhomocysteine Antibody*, Biochemistry 2000, 39, 7255-7265.

Supplemental European Search Report, Aug. 11, 2011.

* cited by examiner

PHARMACEUTICAL COMPOSITIONS FOR THE ADMINISTRATION OF APTAMERS

1. CROSS REFERENCE TO RELATED APPLICATIONS

This application claims the benefit of U.S. provisional application No. 60/736,862, filed Nov. 16, 2005, the contents of which are incorporated herein by reference thereto.

2. STATEMENT REGARDING FEDERALLY SPONSORED RESEARCH OR DEVELOPMENT

Not Applicable.

3. INCORPORATION BY REFERENCE OF MATERIAL SUBMITTED ON A COMPACT DISC

Not Applicable.

4. FIELD OF THE INVENTION

The invention relates to pharmaceutical compositions for administering an aptamer to an animal in need thereof. In one embodiment, the pharmaceutical compositions comprise (i) an aptamer and (ii) an amino acid ester or amide. In another embodiment, the pharmaceutical compositions comprise (i) an aptamer; (ii) a divalent metal cation; and (iii) optionally a carboxylic acid, a phospholipid, a phosphatidyl choline, or a sphingomyelin.

5. BACKGROUND OF THE INVENTION

Aptamers, are oligonucleotides, which can be synthetic or natural, that bind to a particular target molecule, such as a protein or metabolite. Typically, the binding is through interactions other than classic Watson-Crick base pairing.

Aptamers represent a promising class of therapeutic agents currently in pre-clinical and clinical development. Like biologics, e.g., peptides or monoclonal antibodies, aptamers are capable of binding specifically to molecular targets and, through binding, inhibiting target function. A typical aptamer is 10-15 kDa in size (i.e., 30-45 nucleotides), binds its target with sub-nanomolar affinity, and discriminates among closely related targets (e.g., will typically not bind other proteins from the same gene family) (Griffin, et al. (1993), Gene 137(1): 25-31; Jenison, et al. (1998), Antisense Nucleic Acid Drug Dev. 8(4): 265-79; Bell, et al. (1999), In Vitro Cell. Dev. Biol. Anim. 35(9): 533-42; Watson, et al. (2000), Antisense Nucleic Acid Drug Dev. 10(2): 63-75; Daniels, et al. (2002), Anal. Biochem. 305(2): 214-26; Chen, et al. (2003), Proc. Natl. Acad. Sci. U.S.A. 100(16): 9226-31; Khati, et al. (2003), J. Virol. 77(23): 12692-8; Vaish, et al. (2003), Biochemistry 42(29): 8842-51).

Aptamers can be created by an entirely in vitro selection process (Systematic Evaluation of Ligands by Experimental Enrichment, i.e., SELEX™) from libraries of random sequence oligonucleotides as described in U.S. Pat. Nos. 5,475,096 and 5,270,163. Aptamers have been generated against numerous proteins of therapeutic interest, including growth factors, enzymes, immunoglobulins, and receptors (Ellington and Szostak (1990), Nature 346(6287): 818-22; Tuerk and Gold (1990), Science 249(4968): 505-510).

Aptamers have a number of attractive characteristics for use as therapeutics. In addition to high target affinity and specificity, aptamers have shown little or no toxicity or immunogenicity in standard assays (Wlotzka, et al. (2002), Proc. Natl. Acad. Sci. U.S.A. 99(13): 8898-902). Indeed, several therapeutic aptamers have been optimized and advanced through varying stages of pre-clinical development, including pharmacokinetic analysis, characterization of biological efficacy in cellular and animal disease models, and preliminary safety pharmacology assessment (Reyderman and Stavchansky (1998), Pharmaceutical Research 15(6): 904-10; Tucker et al., (1999), J. Chromatography B. 732: 203-212; Watson, et al. (2000), Antisense Nucleic Acid Drug Dev. 10(2): 63-75).

It is important that the pharmacokinetic properties for all oligonucleotide-based therapeutics, including aptamers, be tailored to match the desired pharmaceutical application. While aptamers directed against extracellular targets do not suffer from difficulties associated with intracellular delivery (as is the case with antisense and RNAi-based therapeutics), the aptamer must be distributed to target organs and tissues, and remain in the body (unmodified) for a period of time consistent with the desired dosing regimen. Early work on nucleic acid-based therapeutics has shown that, while unmodified oligonucleotides are degraded rapidly by nuclease digestion, protective modifications at the 2'-position of the sugar, and use of inverted terminal cap structures, e.g., [3'-3'dT], dramatically improve nucleic acid stability in vitro and in vivo (Green, et al. (1995), Chem. Biol. 2(10): 683-95; Jellinek, et al. (1995), Biochemistry 34(36): 11363-72; Ruckman, et al. (1998), J. Biol. Chem. 273(32): 20556-67; Uhlmann, et al. (2000), Methods Enzymol. 313: 268-84). In some SELEX selections (i.e., SELEX experiments or SELEX ions), starting pools of nucleic acids from which aptamers are selected are typically pre-stabilized by chemical modification, for example by incorporation of 2'-fluoropyrimidine (2'-F) substituted nucleotides, to enhance resistance of aptamers against nuclease attack. Aptamers incorporating 2'-O-methylpurine (2'-OMe purine) substituted nucleotides have also been developed through post-SELEX modification steps or, more recently, by enabling synthesis of 2'-OMe-containing random sequence libraries as an integral component of the SELEX process itself.

In addition to clearance by nucleases, oligonucleotide therapeutics are subject to elimination via renal filtration. As such, a nuclease-resistant oligonucleotide administered intravenously exhibits an in vivo half-life of <10 min, unless filtration can be blocked. This can be accomplished by either facilitating rapid distribution out of the blood stream into tissues or by increasing the apparent molecular weight of the oligonucleotide above the effective size cut-off for the glomerulus. Conjugation to a PEG polymer ("PEGylation") can dramatically lengthen residence times of aptamers in circulation, thereby decreasing dosing frequency and enhancing effectiveness against targets. Previous work in animals has examined the plasma pharmacokinetic properties of PEG-conjugated aptamers (Reyderman and Stavchansky (1998), Pharmaceutical Research 15(6): 904-10; Watson, et al. (2000), Antisense Nucleic Acid Drug Dev. 10(2): 63-75)). Determining the extravasation of an aptamer therapeutic, including aptamer therapeutics conjugated to a modifying moiety or containing modified nucleotides and, in particular, determining the potential of aptamers or their modified forms to access diseased tissues (for example, sites of inflammation, or the interior of tumors) define the spectrum of therapeutic opportunities for aptamer intervention.

Typically, therapeutic aptamers are administered by injection, for example, by subcutaneous injection. Accordingly, the aptamer must be dissolved in a liquid vehicle for administration. The relatively high molecular weight of aptamers, and in particular aptamers that have been derivatized, for example by PEGylation, however, often makes it difficult to obtain a pharmaceutical composition wherein the aptamer is dissolved in a pharmaceutically acceptable solvent at a sufficient concentration to provide a pharmaceutical composition that is clinically useful for administration to an animal.

U.S. published application no. 2005/0175708 discloses a composition of matter that permits the sustained delivery of aptamers to a mammal. The aptamers are administered as microspheres that permit sustained release of the aptamers to the site of interest so that the aptamers can exert their biological activity over a prolonged period of time. The aptamers, can be anti-VEGF aptamers.

P. Burmeister et al., (2004), Chemistry and Biology: 15, 25-33 disclose a method for generating a 2'-O-methyl aptamer (ARC245) that binds to vascular endothelial growth factor, which exhibits good stability.

Accordingly, there is a need in the art for improved pharmaceutical compositions, wherein the therapeutic agent is an aptamer. In particular, there is a need for pharmaceutical composition wherein the aptamer can be dissolved in a pharmaceutically acceptable solvent at a sufficient concentration to provide a pharmaceutical composition that is clinically useful for administration to an animal. The present invention addresses this as well as other needs.

Citation of any reference in this application is not to be construed as an admission that such reference is prior art to the present application.

6. SUMMARY OF THE INVENTION

The invention is directed to a pharmaceutical composition comprising:

(i) a salt formed between a protonated aptamer and a pharmaceutically acceptable organic base; and (ii) a pharmaceutically acceptable organic solvent.

In one embodiment, the solvent is a pharmaceutically acceptable organic solvent. In one embodiment, the pharmaceutical composition is a solution of the salt in the pharmaceutically acceptable organic solvent.

The invention also relates to a pharmaceutical composition comprising:

(i) an amino acid ester of formula:

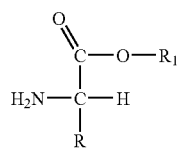

wherein

R is the amino acid side chain; and $R_1$ is a $C_1$ to $C_{22}$ hydrocarbon group; or an amino acid amide of general formula:

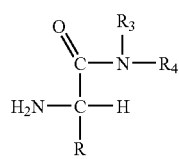

wherein

R is the amino acid side chain;

$R_3$ is a $C_1$ to $C_{22}$ hydrocarbon group; and $R_4$ is hydrogen or a $C_1$ to $C_{22}$ hydrocarbon group; and (ii) a protonated aptamer.

In one embodiment, the amino acid ester or amide is an ester or an amide of lysine and the pharmaceutical composition further comprises one or more of a carboxylic acid, a phospholipid, phosphatidyl choline, or a sphingomyelin.

In one embodiment, the amino acid ester or amide is a diester or diamide of aspartic or glutamic acid.

In one embodiment, the pharmaceutical compositions further comprises a solvent. In one embodiment, the solvent is a pharmaceutically acceptable organic solvent.

The invention also relates to a pharmaceutical compositions comprising (i) an aptamer; and (ii) a divalent metal cation; and (iii) a pharmaceutically acceptable organic solvent.

In one embodiment, the pharmaceutical composition further comprises a carboxylate, a phospholipid, a phosphatidyl choline, or a sphingomyelin.

The invention also relates to methods of administering an aptamer to an animal comprising administering to the animal a pharmaceutical composition of the invention.

The invention also relates to methods of treating or preventing a condition in an animal comprising administering to the animal a pharmaceutical composition of the invention.

7. BRIEF DESCRIPTION OF THE DRAWINGS

FIG. 1. is a graphical representation of the viscosity of pharmaceutical compositions of the invention containing an aptamer at a concentration of 10% (w/v) and 1 equivalent of isoleucine ethanoate, isoleucine butanoate, isoleucine hexanoate, isoleucine octanoate, isoleucine decanoate, isoleucine dodecanoate, or isoleucine hexadecanoate per equivalent of acidic groups on the aptamer dissolved in N-methyl-2-pyrrolidone.

Figure 2:
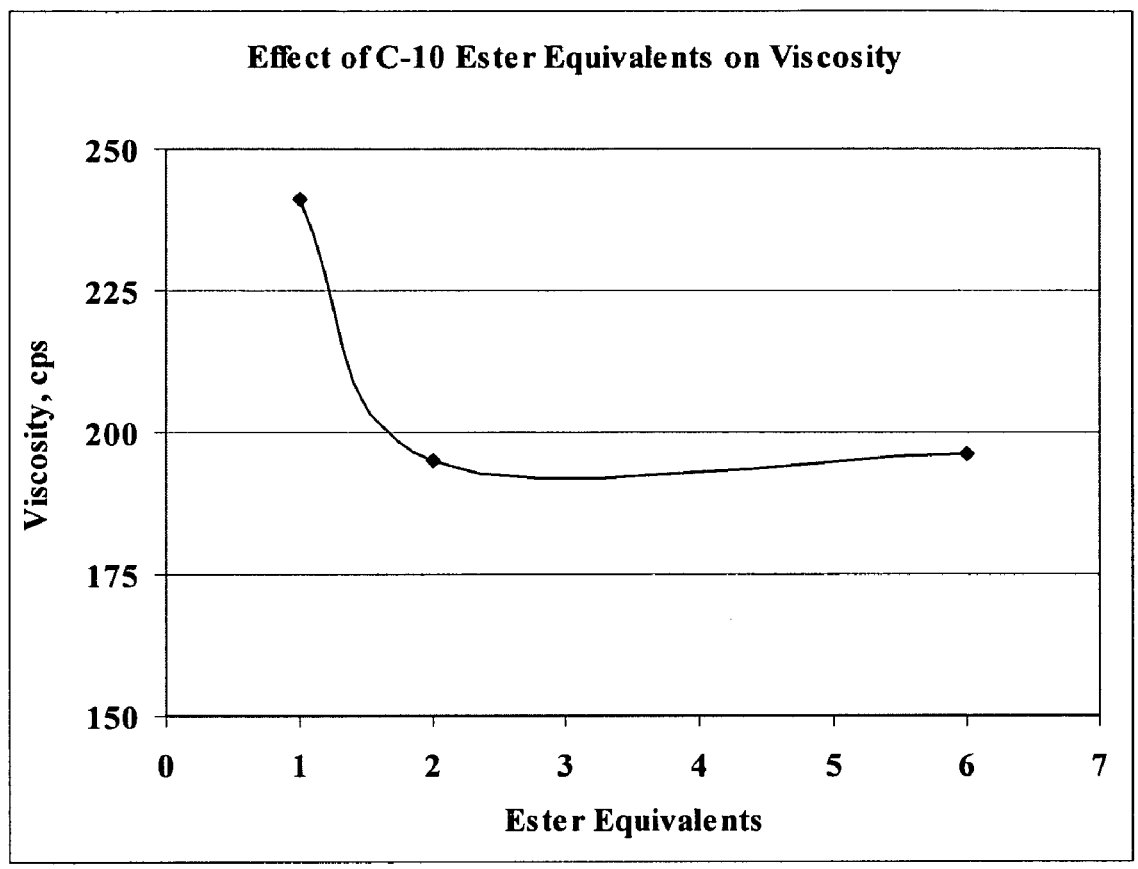

FIG. 2 is a graphical representation of the viscosity of pharmaceutical compositions of the invention containing an aptamer at a concentration of 10% (w/v) and 1, 2, or 6 equivalents of the ester formed between isoleucine decanoate and a per equivalent of acidic functional groups on the aptamer dissolved in N-methyl-2-pyrrolidone.

Figure 3:
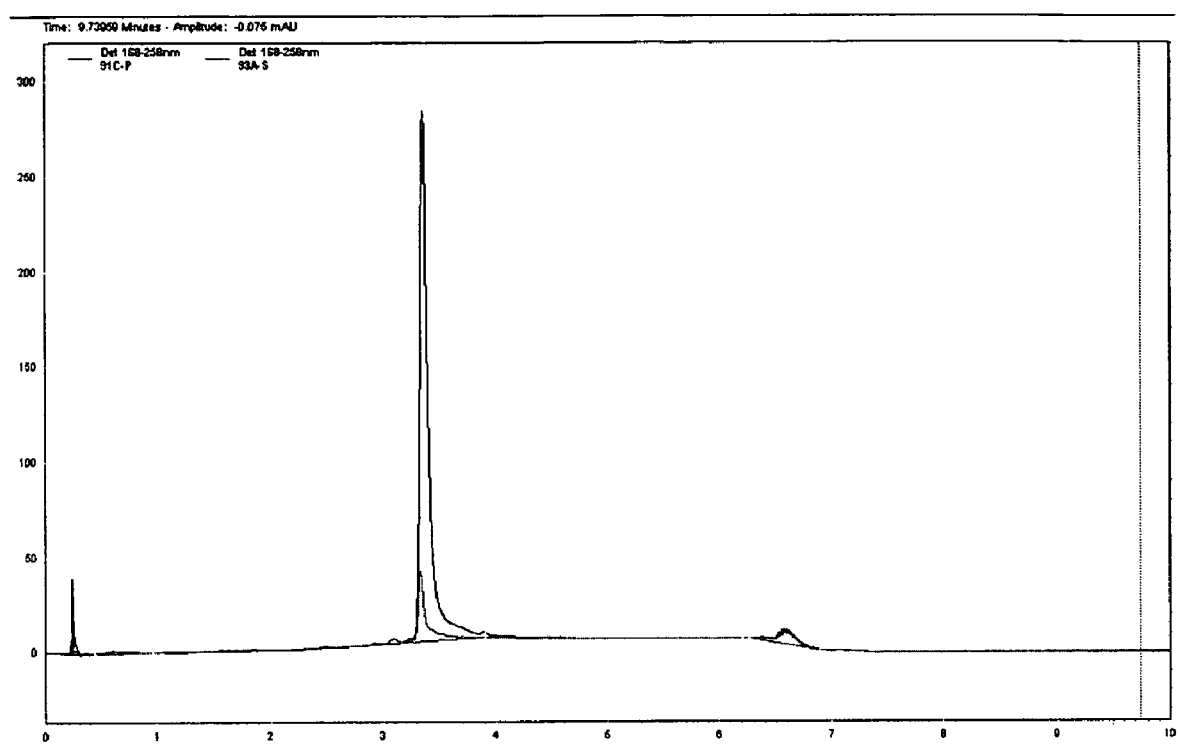

FIG. 3 is an HPLC chromatogram, obtained using the HPLC parameters described in Example 11, of the supernatant (lower trace) and the pellet (upper trace) formed when 50 μL of the pharmaceutical composition of Example 7B containing 10 equivalents of lysine hexadecanoate is injected into 4 mL of water to provide a precipitate and the resulting precipitate and supernatant are separated by centrifugation as described in Example 8.

Figure 4:
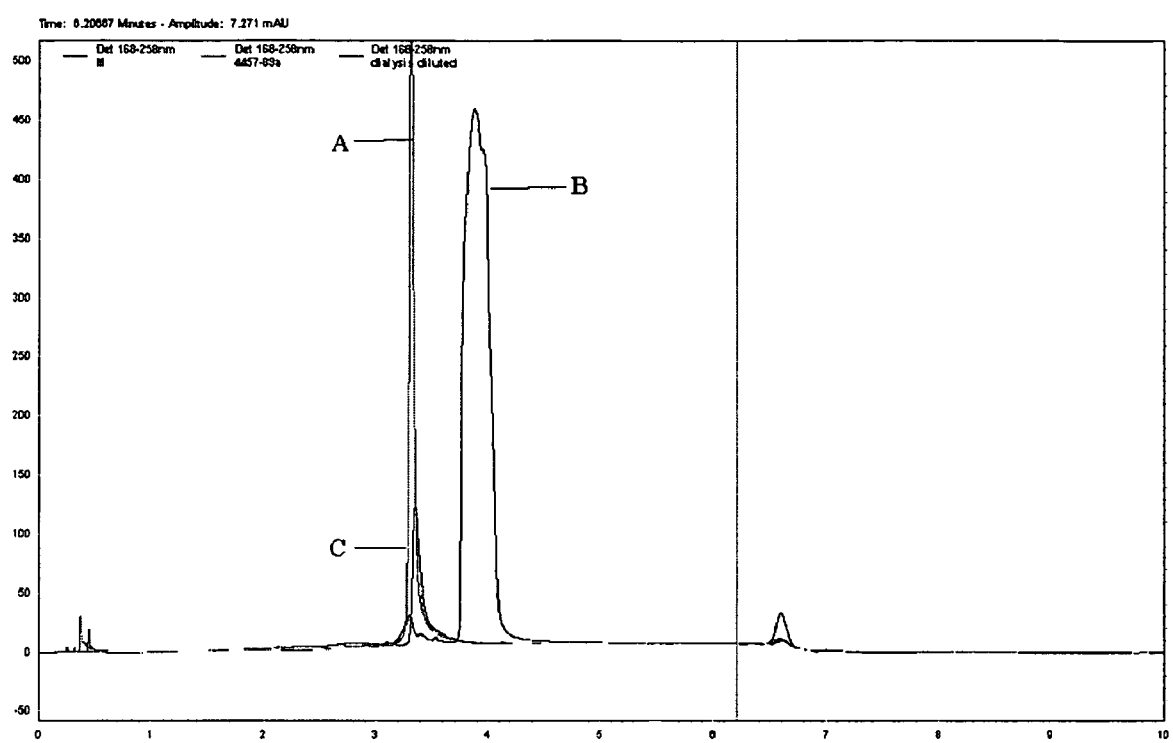

FIG. 4 is an HPLC chromatogram, obtained using the HPLC parameters described in Example 11, of the pharmaceutical composition of Example 7B containing 10 equivalents of lysine hexadecanoate using the basic mobile phase (Trace A) and the acidic mobile phase (Trace B). Trace C is the HPLC chromatogram of the aptamer dissolved in methanol.

8. DETAILED DESCRIPTION OF THE INVENTION

The invention is directed to a pharmaceutical composition comprising:

(i) a salt formed between a protonated aptamer and a pharmaceutically acceptable organic base; and (iii) a pharmaceutically acceptable organic solvent.

In one embodiment, the solvent is a pharmaceutically acceptable organic solvent. In one embodiment, the pharmaceutical composition is a solution of the salt in the pharmaceutically acceptable organic solvent.

In one embodiment, the pharmaceutical compositions comprises:

(i) an amino acid ester or an amino acid amide and (ii) a protonated aptamer.

In one embodiment, the pharmaceutical composition further comprises a solvent. In one embodiment, the solvent is a pharmaceutically acceptable organic solvent.

In one embodiment, the pharmaceutical composition comprises:

(i) an ester or an amide of lysine;

(ii) a protonated aptamer; and (iii) a carboxylic acid.

In one embodiment, the pharmaceutical composition further comprises a solvent. In one embodiment, the solvent is a pharmaceutically acceptable organic solvent.

In one embodiment, the pharmaceutical composition comprises:

(i) an ester or an amide of lysine;

(ii) a protonated aptamer; and (iii) a phospholipid, phosphatidyl choline, or a sphingomyelin.

In one embodiment, the pharmaceutical composition further comprises a solvent. In one embodiment, the solvent is a pharmaceutically acceptable organic solvent.

In one embodiment, the pharmaceutical composition comprises:

(i) a diester or diamide of aspartic or glutamic acid; and (ii) a protonated aptamer.

In one embodiment, the pharmaceutical composition further comprises a solvent. In one embodiment, the solvent is a pharmaceutically acceptable organic solvent.

In another embodiment, the pharmaceutical compositions comprises (i) an aptamer; and (ii) a divalent metal cation; and (iii) a pharmaceutically acceptable organic solvent.

In one embodiment, the pharmaceutical composition further comprises a carboxylate, a phospholipid, a phosphatidyl choline, or a sphingomyelin.

The invention also relates to methods of treating or preventing a condition in an animal comprising administering to the animal a pharmaceutical composition of the invention.

8.1 Definitions

As used herein, the following terms have the following meaning:

The term "aptamer," as used herein, means an oligonucleotide, which can be synthetic or natural, which can bind to a particular target molecule, such as a protein or metabolite, other than by Watson-Crick base pairing and have a pharmacological effect in an animal. Aptamers can be synthesized using conventional phosphodiester linked nucleotides and synthesized using standard solid or solution phase synthesis techniques which are known to those skilled in the art. (See, for example, U.S. Pat. Nos. 5,475,096 and 5,270,163). The binding of aptamers to a target polypeptide can be readily tested by assays known to those skilled in the art. The term "protonated aptamer," as used herein, means an aptamer wherein at least one of the phosphate groups of the aptamer is protonated. In one embodiment, all of the phosphate groups of the aptamer are protonated.

Typically, the pharmacological effect is treating or preventing a condition in an animal.

The term "condition," as used herein means an interruption, cessation, or disorder of a bodily function, system, or organ. Representative conditions include, but are not limited to, diseases such as cancer, inflammation, diabetes, and organ failure.

The phrase "treating," "treatment of," and the like includes the amelioration or cessation of a specified condition.

The phrase "preventing," "prevention of," and the like include the avoidance of the onset of a condition.

"$C_1$-$C_{22}$ hydrocarbon group" means a straight or branched, saturated or unsaturated, cyclic or non-cyclic, aromatic or non-aromatic, carbocyclic or heterocyclic group having from 1 to 22 carbon atoms. Similarly, phrases such as "$C_1$-$C_{22}$ hydrocarbon group," "$C_1$-$C_{16}$ hydrocarbon group," "$C_1$-$C_{10}$ hydrocarbon group," "$C_1$-$C_5$ hydrocarbon group," "$C_1$-$C_3$ hydrocarbon group," "$C_{16}$-$C_{22}$ hydrocarbon group," "$C_8$-$C_{18}$ hydrocarbon group," "$C_{10}$-$C_{18}$ hydrocarbon group," and "$C_{16}$-$C_{18}$ hydrocarbon group" means a straight or branched, saturated or unsaturated, cyclic or non-cyclic, aromatic or non-aromatic, carbocyclic or heterocyclic group having from 1 to 21 carbon atoms, from 1 to 16 carbon atoms, from 1 to 10 carbon atoms, from 1 to 5 carbon atoms, 1 to 3 carbon atoms, 16 to 22 carbon atoms, 8 to 18 carbon atoms, 10 to 18 carbon atoms, and 16 to 18 carbon atoms, respectively. Accordingly, the phrase "an acyl group of formula —C(O)—$R_1$, wherein $R_1$ is a $C_1$ to $C_{21}$ group means an acyl group of formula —C(O)—$R_1$, wherein $R_1$ is a straight or branched, saturated or unsaturated, cyclic or non-cyclic, aromatic or non-aromatic, carbocyclic or heterocyclic hydrocarbon group having from 1 to 21 carbon atoms. Representative acyl groups of formula —C(O)—$R_1$, wherein $R_1$ is an unsubstituted $C_1$ to $C_{21}$ group include, but are not limited to, acetyl, propionyl, butanoyl, hexanoyl, caproyl, laurolyl, myristoyl, palmitoyl, stearoyl, palmioleoyl, oleoyl, linoleoyl, linolenoyl, and benzoyl.

The term "lower alkyl," as used herein means a $C_1$-$C_6$ hydrocarbon group.

The term "salt," as used herein, means two compounds that are not covalently bound but are chemically bound by ionic interactions.

The term "pharmaceutically acceptable," as used herein, when referring to a component of a pharmaceutical composition means that the component, when administered to an animal, does not have undue adverse effects such as excessive toxicity, irritation, or allergic response commensurate with a reasonable benefit/risk ratio. Accordingly, the term "pharmaceutically acceptable organic solvent," as used herein, means an organic solvent that when administered to an animal does not have undue adverse effects such as excessive toxicity, irritation, or allergic response commensurate with a reasonable benefit/risk ratio. Preferably, the pharmaceutically acceptable organic solvent is a solvent that is generally recognized as safe ("GRAS") by the United States Food and Drug Administration ("FDA"). Similarly, the term "pharmaceutically acceptable organic base," as used herein, means an organic base that when administered to an animal does not have undue adverse effects such as excessive toxicity, irritation, or allergic response commensurate with a reasonable benefit/risk ratio.

The term "water miscible organic solvent," as used herein, means an organic solvent that is capable of mixing with water in any ratio without separating into two phases.

The term "water soluble organic solvent," as used herein, means an organic solvent that has a significant level of solubility in water. Typically, a water soluble organic solvent is soluble in water in an amount of at least about 5 percent by weight, preferably at least about 10 percent by weight, more preferably at least about 20 percent by weight, and most preferably at least about 50 percent by weight. For example, triacetin is considered a water soluble solvent since it is soluble in water at a ratio of about 1:14.

The phrase "forms a precipitate," as used herein, means that the pharmaceutical composition forms a precipitate, or solid, when injected into water or into a physiological (in vivo) environment. A precipitate is an insoluble solid formed in a solvent at room temperature in vitro or in a physiological (in vivo) environment. The precipitate can take many forms such as, for example, a solid, a crystal, a gummy mass, or a gel. Preferably, the precipitate is a gummy mass or a gel. A composition of the invention forms a precipitate in water when at least 10% of the composition is retained on a 0.22 µm filter when the composition is mixed with water and filtered at 98° F. Typically, to form the precipitate, about 50 µL to 0.5 mL of the pharmaceutical composition is injected into about 4-5 mL of water. In one embodiment, about 50 µL of the pharmaceutical composition is injected into about 4 mL of water.

The term "fatty acid," as used herein means a carboxylic acid of formula R—C(O)OH, wherein R is a $C_6$-$C_{22}$ linear or branched, saturated or unsaturated, hydrocarbon group. Representative fatty acids include, but are not limited to, caproic acid, lauric acid, myristic acid, palmitic acid, stearic acid, palmic acid, oleic acid, linoleic acid, and linolenic acid.

The term "polycarboxylic acid," as that term is used herein means a polymeric compound having more than one —C(O)OH group. One of ordinary skill in the art would readily recognize polymeric compounds that have more than one —C(O)OH group. Representative polycarboxylic acids include, but are not limited to, hyaluronic acid, polyglutamic acid, polyaspartic acid, and polyacrylic acid.

The phrase "injectable" or "injectable composition," as used herein, means a composition that can be drawn into a syringe and injected subcutaneously, intraperitoneally, or intramuscularly into an animal without causing adverse effects due to the presence of solid material in the composition. Solid materials include, but are not limited to, crystals, gummy masses, and gels. Typically, a formulation or composition is considered to be injectable when no more than about 15%, preferably no more than about 10%, more preferably no more than about 5%, even more preferably no more than about 2%, and most preferably no more than about 1% of the formulation is retained on a 0.22 µm filter when the formulation is filtered through the filter at 98° F. There are, however, some compositions of the invention, which are gels, that can be easily dispensed from a syringe but will be retained on a 0.22 µm filter. In one embodiment, the term "injectable," as used herein, includes these gel compositions. In one embodiment, the term "injectable," as used herein, further includes compositions that when warmed to a temperature of up to about 40° C. and then filtered through a 0.22 µm filter, no more than about 15%, preferably no more than about 10%, more preferably no more than about 5%, even more preferably no more than about 2%, and most preferably no more than about 1% of the formulation is retained on the filter. In one embodiment, an example of an injectable pharmaceutical composition is a solution of a pharmaceutically active compound (for example, an aptamer) in a pharmaceutically acceptable solvent.

The term "solution," as used herein, means a uniformly dispersed mixture at the molecular or ionic level of one or more substances (solute), in one or more other substances (solvent), typically a liquid.

The term "suspension," as used herein, means solid particles that are evenly dispersed in a solvent, which can be aqueous or non-aqueous.

The term "animal," as used herein, includes, but is not limited to, humans, canines, felines, equines, bovines, ovines, porcines, amphibians, reptiles, and avians. Representative animals include, but are not limited to a cow, a horse, a sheep, a pig, an ungulate, a chimpanzee, a monkey, a baboon, a chicken, a turkey, a mouse, a rabbit, a rat, a guinea pig, a dog, a cat, and a human. In one embodiment, the animal is a mammal. In one embodiment, the animal is a human. In one embodiment, the animal is a non-human. In one embodiment, the animal is a canine, a feline, an equine, a bovine, an ovine, or a porcine.

The phrase "drug depot," as used herein means a precipitate, which includes the aptamer, formed within the body of a treated animal that releases the aptamer over time to provide a pharmaceutically effective amount of the aptamer.

The phrase "substantially free of," as used herein, means less than about 2 percent by weight. For example, the phrase "a pharmaceutical composition substantially free of water" means that the amount of water in the pharmaceutical composition is less than about 2 percent by weight of the pharmaceutical composition.

The term "effective amount," as used herein, means an amount sufficient to treat or prevent a condition in an animal.

The term "phospholipid," as used herein, means a compound having the general formula:

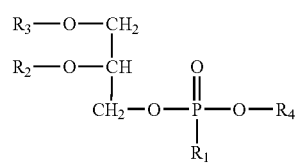

wherein $R_1$ is $O^-$ or —OH;

$R_2$ is:
  (i) —H, or
  (ii) a $C_2$-$C_{36}$ saturated or unsaturated, linear or branched acyl group;

$R_3$ is:
  (i) —H,
  (ii) a $C_2$-$C_{36}$ saturated or unsaturated, linear or branched acyl group; or
  (iii) —C=C—$R_9$ wherein $R_9$ is a $C_1$-$C_{22}$ saturated or unsaturated, linear or branched hydrocarbon group, optionally substituted with one or more nitrogen containing groups;

and at least one of $R_2$ or $R_3$ is not —H;

$R_4$ is:

(i) —H;

(i) —$(CH_2)_n$—$R_5$, wherein $R_5$ is —$N(R_6)(R_7)$ or —$N^+(R_6)(R_7)(R_8)$, $R_6$, $R_7$, and $R_8$ are each independently —H, $C_1$-$C_3$ alkyl group, or $R_6$ and $R_7$ are connected to form a 5- or 6-membered heterocyclic ring with the nitrogen, and n is an integer ranging from 1 to 4, preferably 2;

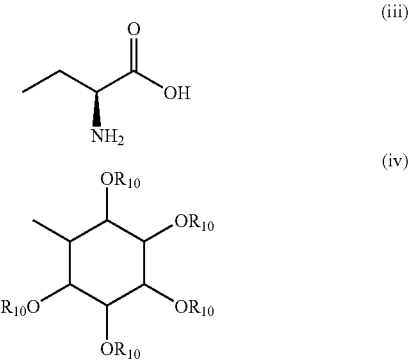

wherein each $R_{10}$ is independently —H or —$P(O)(OH)_2$; or (v) —$CH_2CH(OH)CH_2(OH)$.

The term "saturated or unsaturated, linear or branched $C_2$-$C_{36}$ acyl group," as used herein, means a group of formula —O—C(O)—R, wherein R is a $C_1$-$C_{35}$ hydrocarbon group that can be saturated or unsaturated, linear or branched.

The term "sphingomyelin," as used herein, means a compound having the general formula:

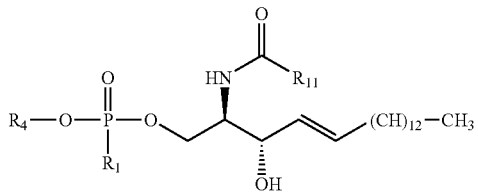

wherein $R_1$ is $O^-$ or —OH;

$R_4$ is:

(i) —H; or (i) —$(CH_2)_n$—$R_5$, wherein $R_5$ is —$N(R_6)(R_7)$ or —$N^+(R_6)(R_7)(R_8)$, $R_6$, $R_7$, and $R_8$ are each independently —H, $C_1$-$C_3$ alkyl, or $R_6$ and $R_7$ are connected to form a 5- or 6-membered heterocyclic ring with the nitrogen, and n is an integer ranging from 1 to 4, preferably 2; and $R_{11}$ is a $C_1$-$C_{22}$ saturated or unsaturated, linear or branched hydrocarbon group optionally substituted with one or more nitrogen containing groups.

The term "about," as used herein to describe a range of values, applies to both the upper limit and the lower limit of the range. For example, the phrase "ranges from about 90:10 to 10:90" has the same meaning as "ranges from about 90:10 to about 10:90."

8.2 The Aptamer

The aptamer can be any aptamer known to those skilled in the art.

In one embodiment, the aptamer is a DNA strand. In one embodiment, the DNA is double stranded DNA. In one embodiment, the DNA is single stranded DNA.

In one embodiment, the aptamer is an RNA strand.

In one embodiment, the aptamer has a molecular weight of up to 80 kD. In one embodiment, the molecular weight of the aptamer ranges from about 15 kD to 80 Kd. In one embodiment, the molecular weight of the aptamer ranges from about 10 kD to 80 Kd. In one embodiment, the molecular weight of the aptamer ranges from about 5 kD to 80 Kd.

In one embodiment, the aptamer has a molecular weight of up to 60 kD. In one embodiment, the molecular weight of the aptamer ranges from about 15 kD to 60 Kd. In one embodiment, the molecular weight of the aptamer ranges from about 10 kD to 60 Kd. In one embodiment, the molecular weight of the aptamer ranges from about 5 kD to 60 Kd.

In one embodiment, the aptamer has a molecular weight of up to 40 kD. In one embodiment, the molecular weight of the aptamer ranges from about 15 kD to 40 Kd. In one embodiment, the molecular weight of the aptamer ranges from about 10 kD to 40 Kd. In one embodiment, the molecular weight of the aptamer ranges from about 5 kD to 40 Kd.

In one embodiment, the aptamer has a molecular weight of up to 30 kD. In one embodiment, the molecular weight of the aptamer ranges from about 15 kD to 30 Kd. In one embodiment, the molecular weight of the aptamer ranges from about 10 kD to 30 Kd. In one embodiment, the molecular weight of the aptamer ranges from about 5 kD to 30 Kd.

In one embodiment, the aptamer has a molecular weight of more than 20 kD. In one embodiment, the molecular weight of the aptamer ranges from about 10 kD to 20 Kd. In one embodiment, the molecular weight of the aptamer ranges from about 5 kD to 20 Kd.

In one embodiment, the molecular weight of the aptamer ranges from about 5 kD to 10 Kd.

The nucleotides that make up the aptamer can be modified to, for example, improve their stability, i.e., improve their in vivo half-life, and/or to reduce their rate of excretion when administered to an animal. The term "modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Modified nucleotides may also include 2' substituted sugars such as 2'-O-methyl-; 2'-O-alkyl; 2'-O-allyl; 2'-S-alkyl; 2'-S-allyl; 2'-fluoro-; 2'-halo or 2'-azido-ribose; carbocyclic sugar analogues; α-anomeric sugars; and epimeric sugars such as arabinose, xyloses or lyxoses, pyranose sugars, furanose sugars, and sedoheptulose.

Modified nucleotides are known in the art and include, but are not limited to, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2 methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; and 1-methylcytosine.

The aptamer can also be modified by replacing one or more phosphodiester linkages with alternative linking groups. Alternative linking groups include, but are not limited to embodiments wherein P(O)O is replaced by P(O)S, P(S)S, P(O)NR$_2$, P(O)R, P(O)OR', CO, or CH$_2$, wherein each R or R' is independently H or a substituted or unsubstituted $C_1$-$C_{20}$ alkyl. A preferred set of R substitutions for the P(O)NR$_2$ group are hydrogen and methoxyethyl. Linking groups are typically attached to each adjacent nucleotide through an —O— bond, but may be modified to include —N— or —S— bonds. Not all linkages in an oligomer need to be identical.

The aptamer can also be modified by conjugating the aptamer to a polymer, for example, to reduce the rate of excretion when administered to an animal. For example, the aptamer can be "PEGylated," i.e., conjugated to polyethylene glycol ("PEG"). In one embodiment, the PEG has an average molecular weight ranging from about 20 kD to 80 kD. Methods to conjugate an aptamer with a polymer, such PEG, are well known to those skilled in the art (See, e.g., Greg T. Hermanson, *Bioconjugate Techniques*, Academic Press, 1966)

As an example of a modified aptamer useful in the compositions and methods of the invention see P. Burmeister et al., *Direct In Vitro Selection of a 2'-O-methyl Aptamer to VEGF*, Chemistry and Biology, vol. 12, 25-33, January 2005.

In one embodiment, the aptamer is conjugated to a polymer.

In one embodiment, the aptamer is an RNA strand that has been conjugated to a polymer.

In one embodiment, the aptamer is an DNA strand that has been conjugated to a polymer.

In one embodiment, the aptamer is conjugated to PEG.

In one embodiment, the aptamer is an RNA strand that has been conjugated to PEG.

In one embodiment, the aptamer is an DNA strand that has been conjugated to PEG.

In one embodiment, the aptamer is a RNA strand wherein at least one of the 2' hydroxyls on the sugars that make up the aptamer are O-methylated.

In one embodiment, the aptamer is a RNA strand wherein at least one of the 2' hydroxyls on the sugars that make up the aptamer are O-methylated and wherein the RNA strand has been conjugated to a polymer.

In one embodiment, the aptamer is a RNA strand wherein at least one of the 2' hydroxyls on the nucleotides that make up the aptamer are O-methylated and wherein the RNA strand has been conjugated to PEG.

In one embodiment, the aptamer is an aptamer that binds to VEGF (vascular endothelial growth factor).

In one embodiment, the aptamer is ARC224 identified in P. Burmeister et al., *Direct In Vitro Selection of a 2'-O-methyl Aptamer to VEGF*, Chemistry and Biology, vol. 12, 25-33, January 2005.

In one embodiment, the aptamer is ARC245 identified in P. Burmeister et al., *Direct In Vitro Selection of a 2'-O-methyl Aptamer to VEGF*, Chemistry and Biology, vol. 12, 25-33, January 2005.

In one embodiment, the aptamer is ARC225 identified in P. Burmeister et al., *Direct In Vitro Selection of a 2'-O-methyl Aptamer to VEGF*, Chemistry and Biology, vol. 12, 25-33, January 2005.

In one embodiment, the aptamer is ARC259 identified in P. Burmeister et al., *Direct In Vitro Selection of a 2'-O-methyl Aptamer to VEGF*, Chemistry and Biology, vol. 12, 25-33, January 2005.

In one embodiment, the aptamer is ARC259 identified in P. Burmeister et al., *Direct In Vitro Selection of a 2'-O-methyl Aptamer to VEGF*, Chemistry and Biology, vol. 12, 25-33, January 2005 wherein the 5' phosphate group of the aptamer has been pegylated with:

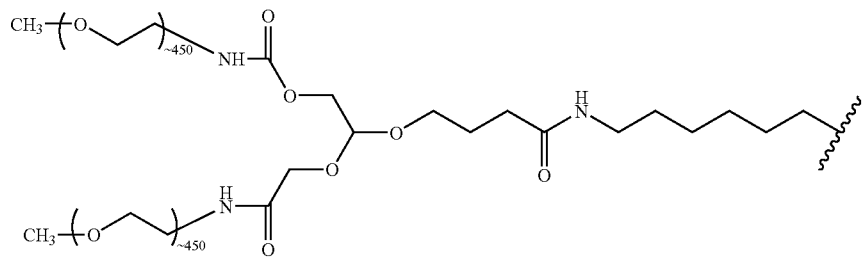

(referred to hereinafter as "pegylated ARC259").

8.3 The Organic Base

Any organic base known to those of ordinary skill in the art can be used in the pharmaceutical compositions of the invention. Preferably, the organic base is a pharmaceutically acceptable organic base. Representative organic bases include, but are not limited to, organic amines including, but are not limited to, ammonia; unsubstituted or hydroxy-substituted mono-, di-, or tri-alkylamines such as cyclohexylamine, cyclopentylamine, cyclohexylamine, dicyclohexylamine; tributyl amine, N-methylamine, N-ethylamine, diethylamine; dimethylamine, triethylamine, mono-, bis-, or tris-(2-hydroxy-lower alkyl amines) (such as mono-, bis-, or tris-(2-hydroxyethyl)amine, 2-hydroxy-tert-butylamine, and tris-(hydroxymethyl)methylamine), N,N,-di-lower alkyl-N-

(hydroxy lower alkyl)-amines (such as N,N,-dimethyl-N-(2-hydroxyethyl)amine or N,N-dialkyl-N-tris-(2-hydroxyethyl)amines)); pyridine; benzylamine; phenethylamine; N-methyl-D-glucamine; N,N'-dibenzylethylenediamine; chloroprocaine; choline; procaine, and amino acids such as arginine, lysine (See, also, Berge et al., *J. Pharm. Sci.,* 1977, 66, 1).

The invention also contemplates pharmaceutical compositions comprising a salt formed between the aptamer and a metal ion, such as sodium, lithium, or potassium ion, and a pharmaceutically acceptable organic solvent. Typically, these compositions are useful when a low concentration, generally less than about 25 mg/mL, of the aptamer in the pharmaceutically acceptable organic solvent is sufficient.

In one embodiment, the amine is an amino acid ester.

In one embodiment, the amine is an amino acid amide.

In one embodiment, the amine is a diamine (for example, N,N'-dibenzylethylenediamine or an ester or amide of lysine).

In one embodiment, the amine is a diamine and the pharmaceutical composition further comprises a carboxylic acid, a phospholipid, a sphingomyelin, or phosphatidyl choline.

8.3.1 The Amino Acid Ester

The amino acid esters can be any ester of any amino acid, i.e., an amino acid wherein the carboxylic acid group of the amino acid is esterified with a $C_1$-$C_{22}$ alcohol. Accordingly, the amino acid esters have the general formula (I):

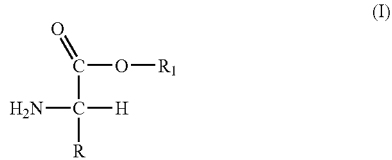

wherein

R is the amino acid side chain; and $R_1$ is a $C_1$ to $C_{22}$ hydrocarbon group.

As one of ordinary skill in the art would readily know, a wide variety of groups are possible for the amino acid side, R. For example, the amino acid side can be a hydrocarbon group that can be optionally substituted. Suitable substituents include, but are not limited to, halo, nitro, cyano, thiol, amino, hydroxy, carboxylic acid, sulfonic acid, aromatic group, and aromatic or non-aromatic heterocyclic group. Preferably the amino acid side chain is a $C_1$-$C_{10}$ straight or branched chain hydrocarbon, optionally substituted with a thiol, amino, hydroxy, carboxylic acid, aromatic group, or aromatic or non-aromatic heterocyclic group.

The amino acid ester can be an ester of a naturally occurring amino acid or a synthetically prepared amino acid. The amino acid can be a D-amino acid or an L-amino acid. Preferably, the amino acid ester is the ester of a naturally occurring amino acid. More, preferably, the amino acid ester is an ester of an amino acid selected from glycine, alanine, valine, leucine, isoleucine, phenylalanine, asparagine, glutamine, tryptophane, proline, serine, threonine, tyrosine, hydroxyproline, cysteine, methionine, aspartic acid, glutamic acid, lysine, arginine, and histidine.

The hydrocarbon group, $R_1$, can be any $C_1$ to $C_{22}$ hydrocarbon group. Representative $C_1$ to $C_{22}$ hydrocarbon groups include, but are not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, allyl, cyclopentyl, cyclohexyl, cis-9-hexadecenyl, cis-9-octadecenyl, cis, cis-9,12-octadecenyl, and cis, cis, cis-9,12,15-octadecatrienyl.

In one embodiment, $R_1$ is a straight chain hydrocarbon group.

In one embodiment, $R_1$ is a branched chain hydrocarbon group.

In one embodiment, $R_1$ is a saturated hydrocarbon group.

In one embodiment, $R_1$ is an unsaturated hydrocarbon group.

In one embodiment, $R_1$ is a straight chain, saturated hydrocarbon group.

In one embodiment, $R_1$ is a straight chain, unsaturated hydrocarbon group.

In one embodiment, $R_1$ is a $C_1$-$C_{16}$ hydrocarbon group.

In one embodiment, $R_1$ is a $C_1$-$C_{10}$ hydrocarbon group.

In one embodiment, $R_1$ is a $C_1$-$C_5$ hydrocarbon group.

In one embodiment, $R_1$ is a $C_1$-$C_3$ hydrocarbon group.

In one embodiment, $R_1$ is a $C_6$-$C_{22}$ hydrocarbon group.

In one embodiment, $R_1$ is a $C_6$-$C_{18}$ hydrocarbon group.

In one embodiment, $R_1$ is a $C_8$-$C_{18}$ hydrocarbon group.

In one embodiment, $R_1$ is a $C_{10}$-$C_{18}$ hydrocarbon group.

In one embodiment, $R_1$ is a $C_{16}$-$C_{18}$ hydrocarbon group.

In one embodiment, $R_1$ is a $C_{16}$-$C_{22}$ hydrocarbon group.

In one embodiment, $R_1$ is a $C_1$-$C_{16}$ straight chain hydrocarbon group.

In one embodiment, $R_1$ is a $C_1$-$C_{10}$ straight chain hydrocarbon group.

In one embodiment, $R_1$ is a $C_1$-$C_5$ straight chain hydrocarbon group.

In one embodiment, $R_1$ is a $C_1$-$C_3$ straight chain hydrocarbon group.

In one embodiment, $R_1$ is a $C_6$-$C_{22}$ straight chain hydrocarbon group.

In one embodiment, $R_1$ is a $C_6$-$C_{18}$ straight chain hydrocarbon group.

In one embodiment, $R_1$ is a $C_8$-$C_{18}$ straight chain hydrocarbon group.

In one embodiment, $R_1$ is a $C_{10}$-$C_{18}$ straight chain hydrocarbon group.

In one embodiment, $R_1$ is a $C_{16}$-$C_{18}$ straight chain hydrocarbon group.

In one embodiment, $R_1$ is a $C_{16}$-$C_{22}$ straight chain hydrocarbon group.

In one embodiment, $R_1$ is a $C_1$-$C_{16}$ branched chain hydrocarbon group.

In one embodiment, $R_1$ is a $C_1$-$C_{10}$ branched chain hydrocarbon group.

In one embodiment, $R_1$ is a $C_1$-$C_5$ branched chain hydrocarbon group.

In one embodiment, $R_1$ is a $C_1$-$C_3$ branched chain hydrocarbon group.

In one embodiment, $R_1$ is a $C_6$-$C_{22}$ branched chain hydrocarbon group.

In one embodiment, $R_1$ is a $C_6$-$C_{18}$ branched chain hydrocarbon group.

In one embodiment, $R_1$ is a $C_8$-$C_{18}$ branched chain hydrocarbon group.

In one embodiment, $R_1$ is a $C_{10}$-$C_{18}$ branched chain hydrocarbon group.

In one embodiment, $R_1$ is a $C_{16}$-$C_{18}$ branched chain hydrocarbon group.

In one embodiment, $R_1$ is a $C_{16}$-$C_{22}$ branched chain hydrocarbon group.

In one embodiment, $R_1$ is a $C_1$-$C_{16}$ straight chain unsaturated hydrocarbon group.

In one embodiment, $R_1$ is a $C_1$-$C_{10}$ straight chain unsaturated hydrocarbon group.

In one embodiment, $R_1$ is a $C_1$-$C_5$ straight chain unsaturated hydrocarbon group.

In one embodiment, $R_1$ is a $C_1$-$C_3$ straight chain unsaturated hydrocarbon group.

In one embodiment, $R_1$ is a $C_6$-$C_{22}$ straight chain unsaturated hydrocarbon group.

In one embodiment, $R_1$ is a $C_6$-$C_{18}$ straight chain unsaturated hydrocarbon group.

In one embodiment, $R_1$ is a $C_8$-$C_{18}$ straight chain unsaturated hydrocarbon group.

In one embodiment, $R_1$ is a $C_{10}$-$C_{18}$ straight chain unsaturated hydrocarbon group.

In one embodiment, $R_1$ is a $C_{16}$-$C_{18}$ straight chain unsaturated hydrocarbon group.

In one embodiment, $R_1$ is a $C_{16}$-$C_{22}$ straight chain unsaturated hydrocarbon group.

As discussed later, by varying the structure of $R_1$ it is possible to vary the properties of the pharmaceutical compositions.

The amino acid esters can be obtained by esterifying an amino acid with an alcohol of formula $R_1$—OH using methods well known to those skilled in the art such as those described in J. March, *Advanced Organic Chemistry, Reaction Mechanisms and Structure*, 4th ed. John Wiley & Sons, NY, 1992, pp. 393-400. The amino acids and alcohols of formula $R_1$—OH are commercially available or can be prepared by methods well known to those skilled in the art. When esterifying the amino acid with the alcohol of formula $R_1$—OH, it may be necessary to protect some other functional group of the amino acid or the alcohol with a protecting group that is subsequently removed after the esterification reaction. One of ordinary skill in the art would readily know what functional groups would need to be protected before esterifying the amino acid with the alcohol of formula $R_1$—OH. Suitable protecting groups are known to those skilled in the art such as those described in T. W. Greene, et al. *Protective Groups in Organic Synthesis*, 3rd ed. (1999).

8.3.1 The Amino Acid Amide

The amino acid amides can be any amide of any amino acid, i.e., an amino acid wherein the carboxylic acid group of the amino acid is reacted with an amine of formula $HN(R_3)(R_4)$, wherein $R_3$ and $R_4$ are defined above, to provide an amide. Accordingly, the amino acid amides have the general formula (II):

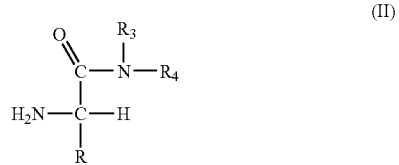

(II)

wherein

R is the amino acid side chain;

$R_3$ is a $C_1$ to $C_{22}$ hydrocarbon group; and $R_4$ is hydrogen or a $C_1$ to $C_{22}$ hydrocarbon group.

As one of ordinary skill in the art would readily know, a wide variety of groups are possible for the amino acid side, R. For example, the amino acid side can be a hydrocarbon group that can be optionally substituted. Suitable substituents include, but are not limited to, halo, nitro, cyano, thiol, amino, hydroxy, carboxylic acid, sulfonic acid, aromatic group, and aromatic or non-aromatic heterocyclic group. Preferably the amino acid side chain is a $C_1$-$C_{10}$ straight or branched chain hydrocarbon, optionally substituted with a thiol, amino, hydroxy, carboxylic acid, aromatic group, or aromatic or non-aromatic heterocyclic group; an aromatic group, or an aromatic or non-aromatic heterocyclic group.

The amino acid amide can be an amide of a naturally occurring amino acid or a synthetically prepared amino acid. The amino acid can be a D-amino acid or an L-amino acid. Preferably, the amino acid ester is the ester of a naturally occurring amino acid. More, preferably, the amino acid ester is an ester of an amino acid selected from glycine, alanine, valine, leucine, isoleucine, phenylalanine, asparagine, glutamine, tryptophane, proline, serine, threonine, tyrosine, hydroxyproline, cysteine, methionine, aspartic acid, glutamic acid, lysine, arginine, and histidine.

The $R_3$ group can be any $C_1$ to $C_{22}$ hydrocarbon group. The $R_4$ group can be hydrogen or any $C_1$ to $C_{22}$ hydrocarbon group. Representative $C_1$ to $C_{22}$ hydrocarbon groups include, but are not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, allyl, cyclopentyl, cyclohexyl, cis-9-hexadecenyl, cis-9-octadecenyl, cis, cis-9,12-octadecenyl, and cis, cis, cis-9,12,15-octadecatrienyl.

In one embodiment, $R_4$ is hydrogen and $R_3$ is a straight chain hydrocarbon group.

In one embodiment, $R_4$ is hydrogen and $R_3$ is a branched chain hydrocarbon group.

In one embodiment, $R_4$ is hydrogen and $R_3$ is a saturated hydrocarbon group.

In one embodiment, $R_4$ is hydrogen and $R_3$ is an unsaturated hydrocarbon group.

In one embodiment, $R_4$ is hydrogen and $R_3$ is a straight chain, saturated hydrocarbon group.

In one embodiment, $R_4$ is hydrogen and $R_3$ is a straight chain, unsaturated hydrocarbon group.

In one embodiment, $R_4$ is hydrogen and $R_3$ is a $C_1$-$C_{16}$ hydrocarbon group.

In one embodiment, $R_4$ is hydrogen and $R_3$ is a $C_1$-$C_{10}$ hydrocarbon group.

In one embodiment, $R_4$ is hydrogen and $R_3$ is a $C_1$-$C_5$ hydrocarbon group.

In one embodiment, $R_4$ is hydrogen and $R_3$ is a $C_1$-$C_3$ hydrocarbon group.

In one embodiment, $R_4$ is hydrogen and $R_3$ is a $C_6$-$C_{22}$ hydrocarbon group.

In one embodiment, $R_4$ is hydrogen and $R_3$ is a $C_6$-$C_{18}$ hydrocarbon group.

In one embodiment, $R_4$ is hydrogen and $R_3$ is a $C_8$-$C_{18}$ hydrocarbon group.

In one embodiment, $R_4$ is hydrogen and $R_3$ is a $C_{10}$-$C_{18}$ hydrocarbon group.

In one embodiment, $R_4$ is hydrogen and $R_3$ is a $C_{16}$-$C_{18}$ hydrocarbon group.

In one embodiment, $R_4$ is hydrogen and $R_3$ is a $C_{16}$-$C_{22}$ hydrocarbon group.

In one embodiment, $R_4$ is hydrogen and $R_3$ is a $C_1$-$C_{16}$ straight chain hydrocarbon group.

In one embodiment, $R_4$ is hydrogen and $R_3$ is a $C_1$-$C_{10}$ straight chain hydrocarbon group.

In one embodiment, $R_4$ is hydrogen and $R_3$ is a $C_1$-$C_5$ straight chain hydrocarbon group.

In one embodiment, $R_4$ is hydrogen and $R_3$ is a $C_1$-$C_3$ straight chain hydrocarbon group.

In one embodiment, $R_4$ is hydrogen and $R_3$ is a $C_6$-$C_{22}$ straight chain hydrocarbon group.

In one embodiment, $R_4$ is hydrogen and $R_3$ is a $C_6$-$C_{18}$ straight chain hydrocarbon group.

In one embodiment, $R_4$ is hydrogen and $R_3$ is a $C_8$-$C_{18}$ straight chain hydrocarbon group.

In one embodiment, $R_4$ is hydrogen and $R_3$ is a $C_{10}$-$C_{18}$ straight chain hydrocarbon group.

In one embodiment, $R_4$ is hydrogen and $R_3$ is a $C_{16}$-$C_{18}$ straight chain hydrocarbon group.

In one embodiment, $R_4$ is hydrogen and $R_3$ is a $C_{16}$-$C_{22}$ straight chain hydrocarbon group.

In one embodiment, $R_4$ is hydrogen and $R_3$ is a $C_1$-$C_{16}$ branched chain hydrocarbon group.

In one embodiment, $R_4$ is hydrogen and $R_3$ is a $C_1$-$C_{10}$ branched chain hydrocarbon group.

In one embodiment, $R_4$ is hydrogen and $R_3$ is a $C_1$-$C_5$ branched chain hydrocarbon group.

In one embodiment, $R_4$ is hydrogen and $R_3$ is a $C_1$-$C_3$ branched chain hydrocarbon group.

In one embodiment, $R_4$ is hydrogen and $R_3$ is a $C_6$-$C_{22}$ branched chain hydrocarbon group.

In one embodiment, $R_4$ is hydrogen and $R_3$ is a $C_6$-$C_{18}$ branched chain hydrocarbon group.

In one embodiment, $R_4$ is hydrogen and $R_3$ is a $C_8$-$C_{18}$ branched chain hydrocarbon group.

In one embodiment, $R_4$ is hydrogen and $R_3$ is a $C_{10}$-$C_{18}$ branched chain hydrocarbon group.

In one embodiment, $R_4$ is hydrogen and $R_3$ is a $C_{16}$-$C_{18}$ branched chain hydrocarbon group.

In one embodiment, $R_4$ is hydrogen and $R_3$ is a $C_{16}$-$C_{22}$ branched chain hydrocarbon group.

In one embodiment, $R_4$ is hydrogen and $R_3$ is a $C_1$-$C_{16}$ straight chain saturated hydrocarbon group.

In one embodiment, $R_4$ is hydrogen and $R_3$ is a $C_1$-$C_{10}$ straight chain saturated hydrocarbon group.

In one embodiment, $R_4$ is hydrogen and $R_3$ is a $C_1$-$C_5$ straight chain saturated hydrocarbon group.

In one embodiment, $R_4$ is hydrogen and $R_3$ is a $C_1$-$C_3$ straight chain saturated hydrocarbon group.

In one embodiment, $R_4$ is hydrogen and $R_3$ is a $C_6$-$C_{22}$ straight chain saturated hydrocarbon group.

In one embodiment, $R_4$ is hydrogen and $R_3$ is a $C_6$-$C_{18}$ straight chain saturated hydrocarbon group.

In one embodiment, $R_4$ is hydrogen and $R_3$ is a $C_8$-$C_{18}$ straight chain saturated hydrocarbon group.

In one embodiment, $R_4$ is hydrogen and $R_3$ is a $C_{10}$-$C_{18}$ straight chain saturated hydrocarbon group.

In one embodiment, $R_4$ is hydrogen and $R_3$ is a $C_{16}$-$C_{18}$ straight chain saturated hydrocarbon group.

In one embodiment, $R_4$ is hydrogen and $R_3$ is a $C_{16}$-$C_{22}$ straight chain saturated hydrocarbon group.

In one embodiment, each of $R_3$ and $R_4$ are a straight or branched chain, saturated or unsaturated hydrocarbon group, wherein $R_3$ and $R_4$ may be the same or different.

In one embodiment, each of $R_3$ and $R_4$ are a $C_1$-$C_{16}$ hydrocarbon group, wherein $R_3$ and $R_4$ may be the same or different.

In one embodiment, each of $R_3$ and $R_4$ are a $C_1$-$C_{10}$ hydrocarbon group, wherein $R_3$ and $R_4$ may be the same or different.

In one embodiment, each of $R_3$ and $R_4$ are a $C_1$-$C_5$ hydrocarbon group, wherein $R_3$ and $R_4$ may be the same or different.

In one embodiment, each of $R_3$ and $R_4$ are a $C_1$-$C_3$ hydrocarbon group, wherein $R_3$ and $R_4$ may be the same or different.

In one embodiment, each of $R_3$ and $R_4$ are a $C_6$-$C_{22}$ hydrocarbon group, wherein $R_3$ and $R_4$ may be the same or different.

In one embodiment, each of $R_3$ and $R_4$ are a $C_6$-$C_{18}$ hydrocarbon group, wherein $R_3$ and $R_4$ may be the same or different.

In one embodiment, each of $R_3$ and $R_4$ are a $C_8$-$C_{18}$ hydrocarbon group, wherein $R_3$ and $R_4$ may be the same or different.

In one embodiment, each of $R_3$ and $R_4$ are a $C_{10}$-$C_{18}$ hydrocarbon group, wherein $R_3$ and $R_4$ may be the same or different.

In one embodiment, each of $R_3$ and $R_4$ are a $C_{16}$-$C_{18}$ hydrocarbon group, wherein $R_3$ and $R_4$ may be the same or different.

In one embodiment, each of $R_3$ and $R_4$ are a $C_{16}$-$C_{22}$ hydrocarbon group, wherein $R_3$ and $R_4$ may be the same or different.

In one embodiment, each of $R_3$ and $R_4$ are a $C_1$-$C_{16}$ straight chain hydrocarbon group, wherein $R_3$ and $R_4$ may be the same or different.

In one embodiment, each of $R_3$ and $R_4$ are a $C_1$-$C_{10}$ straight chain hydrocarbon group, wherein $R_3$ and $R_4$ may be the same or different.

In one embodiment, each of $R_3$ and $R_4$ are a $C_1$-$C_5$ straight chain hydrocarbon group, wherein $R_3$ and $R_4$ may be the same or different.

In one embodiment, each of $R_3$ and $R_4$ are a $C_1$-$C_3$ straight chain hydrocarbon group, wherein $R_3$ and $R_4$ may be the same or different.

In one embodiment, each of $R_3$ and $R_4$ are a $C_6$-$C_{22}$ straight chain hydrocarbon group, wherein $R_3$ and $R_4$ may be the same or different.

In one embodiment, each of $R_3$ and $R_4$ are a $C_6$-$C_{18}$ straight chain hydrocarbon group, wherein $R_3$ and $R_4$ may be the same or different.

In one embodiment, each of $R_3$ and $R_4$ are a $C_8$-$C_{18}$ straight chain hydrocarbon group, wherein $R_3$ and $R_4$ may be the same or different.

In one embodiment, each of $R_3$ and $R_4$ are a $C_{10}$-$C_{18}$ straight chain hydrocarbon group, wherein $R_3$ and $R_4$ may be the same or different.

In one embodiment, each of $R_3$ and $R_4$ are a $C_{16}$-$C_{18}$ straight chain hydrocarbon group, wherein $R_3$ and $R_4$ may be the same or different.

In one embodiment, each of $R_3$ and $R_4$ are a $C_{16}$-$C_{22}$ straight chain hydrocarbon group, wherein $R_3$ and $R_4$ may be the same or different.

In one embodiment, each of $R_3$ and $R_4$ are a $C_1$-$C_{16}$ branched chain hydrocarbon group, wherein $R_3$ and $R_4$ may be the same or different.

In one embodiment, each of $R_3$ and $R_4$ are a $C_1$-$C_{10}$ branched chain hydrocarbon group, wherein $R_3$ and $R_4$ may be the same or different.

In one embodiment, each of $R_3$ and $R_4$ are a $C_1$-$C_5$ branched chain hydrocarbon group, wherein $R_3$ and $R_4$ may be the same or different.

In one embodiment, each of $R_3$ and $R_4$ are a $C_1$-$C_3$ branched chain hydrocarbon group, wherein $R_3$ and $R_4$ may be the same or different.

In one embodiment, each of $R_3$ and $R_4$ are a $C_6$-$C_{22}$ branched chain hydrocarbon group, wherein $R_3$ and $R_4$ may be the same or different.

In one embodiment, each of $R_3$ and $R_4$ are a $C_6$-$C_{18}$ branched chain hydrocarbon group, wherein $R_3$ and $R_4$ may be the same or different.

In one embodiment, each of $R_3$ and $R_4$ are a $C_8$-$C_{18}$ branched chain hydrocarbon group, wherein $R_3$ and $R_4$ may be the same or different.

In one embodiment, each of $R_3$ and $R_4$ are a $C_{10}$-$C_{18}$ branched chain hydrocarbon group, wherein $R_3$ and $R_4$ may be the same or different.

In one embodiment, each of $R_3$ and $R_4$ are a $C_{16}$-$C_{18}$ branched chain hydrocarbon group, wherein $R_3$ and $R_4$ may be the same or different.

In one embodiment, each of $R_3$ and $R_4$ are a $C_{16}$-$C_{22}$ branched chain hydrocarbon group, wherein $R_3$ and $R_4$ may be the same or different.

In one embodiment, each of $R_3$ and $R_4$ are a $C_1$-$C_{16}$ straight chain saturated hydrocarbon group, wherein $R_3$ and $R_4$ may be the same or different.

In one embodiment, each of $R_3$ and $R_4$ are a $C_1$-$C_{10}$ straight chain saturated hydrocarbon group, wherein $R_3$ and $R_4$ may be the same or different.

In one embodiment, each of $R_3$ and $R_4$ are a $C_1$-$C_5$ straight chain saturated hydrocarbon group, wherein $R_3$ and $R_4$ may be the same or different.

In one embodiment, each of $R_3$ and $R_4$ are a $C_1$-$C_3$ straight chain saturated hydrocarbon group, wherein $R_3$ and $R_4$ may be the same or different.

In one embodiment, each of $R_3$ and $R_4$ are a $C_6$-$C_{22}$ straight chain saturated hydrocarbon group, wherein $R_3$ and $R_4$ may be the same or different.

In one embodiment, each of $R_3$ and $R_4$ are a $C_6$-$C_{18}$ straight chain saturated hydrocarbon group, wherein $R_3$ and $R_4$ may be the same or different.

In one embodiment, each of $R_3$ and $R_4$ are a $C_8$-$C_{18}$ straight chain saturated hydrocarbon group, wherein $R_3$ and $R_4$ may be the same or different.

In one embodiment, each of $R_3$ and $R_4$ are a $C_{10}$-$C_{18}$ straight chain saturated hydrocarbon group, wherein $R_3$ and $R_4$ may be the same or different.

In one embodiment, each of $R_3$ and $R_4$ are a $C_{16}$-$C_{18}$ straight chain saturated hydrocarbon group, wherein $R_3$ and $R_4$ may be the same or different.

In one embodiment, each of $R_3$ and $R_4$ are a $C_{16}$-$C_{22}$ straight chain saturated hydrocarbon group, wherein $R_3$ and $R_4$ may be the same or different.

In one embodiment, the combined number of carbon atoms in $R_3$ and $R_4$ is at least 6. In one embodiment, the combined number of carbon atoms in $R_3$ and $R_4$ is at least 8. In one embodiment, the combined number of carbon atoms in $R_3$ and $R_4$ is at least 10. In one embodiment, the combined number of carbon atoms in $R_3$ and $R_4$ is at least 12. In one embodiment, the combined number of carbon atoms in $R_3$ and $R_4$ is at least 18.

In one embodiment, the combined number of carbon atoms in $R_3$ and $R_4$ is less than 6. In one embodiment, the combined number of carbon atoms in $R_3$ and $R_4$ is less than 8. In one embodiment, the combined number of carbon atoms in $R_3$ and $R_4$ is less than 10. In one embodiment, the combined number of carbon atoms in $R_3$ and $R_4$ is less than 12. In one embodiment, the combined number of carbon atoms in $R_3$ and $R_4$ is less than 18.

In one embodiment, the combined number of carbon atoms in $R_3$ and $R_4$ ranges from about 1 to 16. In one embodiment, the combined number of carbon atoms in $R_3$ and $R_4$ ranges from about 1 to 10. In one embodiment, the combined number of carbon atoms in $R_3$ and $R_4$ ranges from about 1 to 5. In one embodiment, the combined number of carbon atoms in $R_3$ and $R_4$ ranges from about 1 to 3. In one embodiment, the combined number of carbon atoms in $R_3$ and $R_4$ ranges from about 16 to 22. In one embodiment, the combined number of carbon atoms in $R_3$ and $R_4$ ranges from about 16 to 18. In one embodiment, the combined number of carbon atoms in $R_3$ and $R_4$ ranges from about 8 to 18. In one embodiment, the combined number of carbon atoms in $R_3$ and $R_4$ ranges from about 10 to 18. In one embodiment, the combined number of carbon atoms in $R_3$ and $R_4$ ranges from about 12 to 18. In one embodiment, the combined number of carbon atoms in $R_3$ and $R_4$ ranges from about 6 to 30. In one embodiment, the combined number of carbon atoms in $R_3$ and $R_4$ ranges from about 22 to 30.

As discussed later, by varying the structure of $R_3$ and $R_4$ it is possible to vary the properties of the pharmaceutical compositions.

The amino acid amides can be obtained by converting the carboxylic acid group of the amino acid to an amide group using methods well known to those skilled in the art such as those described in J. March, *Advanced Organic Chemistry, Reaction Mechanisms and Structure*, 4$^{th}$ ed. John Wiley & Sons, NY, 1992, pp. 417-427. Typically, the amino acid is converted to an amino acid derivative such as an amino acid ester or an acid chloride of the amino acid and the amino acid derivative is then reacted with an amine of formula $NHR_3R_4$ to provide the amino acid amide. The amino acids and amines of formula $NHR_3R_4$ are commercially available or can be prepared by methods well known to those skilled in the art. When forming the derivative of the amino acid or reacting the amino acid derivative with an amine of formula $NHR_3R_4$, it may be necessary to protect some other functional group of the amino acid derivative or the amine with a protecting group that is subsequently removed after the amidation reaction. One of ordinary skill in the art would readily know what functional groups would need to be protected before reacting the derivative of the amino acid with the amine of formula $NHR_3R_4$. Suitable protecting groups are known to those skilled in the art such as those described in T. W. Greene, et al. *Protective Groups in Organic Synthesis*, 3$^{rd}$ ed. (1999).

8.4 Examples of Pharmaceutical Compositions of the Invention

8.4.1 Pharmaceutical Compositions Comprising (i) a Pharmaceutically Acceptable Organic Base and (ii) a Protonated Aptamer In one embodiment, the pharmaceutical composition comprises (i) a protonated aptamer and an (ii) a pharmaceutically acceptable organic base. Without wishing to be bound by theory, it is believed that the acidic phosphate groups of the a protonated aptamer protonate the amine group of the pharmaceutically acceptable organic base to form a salt between one or more pharmaceutically acceptable organic base molecules and the aptamer as illustrated schematically below for a pharmaceutically acceptable organic base of formula Base-$NH_2$ and a protonated aptamer.

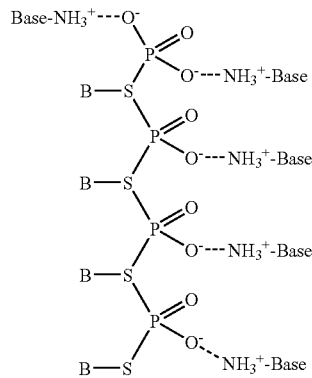

wherein B is a nucleotide, S is a sugar, and Base-NH$_3^+$ is a protonated pharmaceutically acceptable organic base. It is not necessary, however, that every phosphate group be ionically bound to a pharmaceutically acceptable organic base molecule.

Any pharmaceutically acceptable organic base described above can be used in the pharmaceutical compositions.

Any aptamer described above can be used in the pharmaceutical compositions.

In one embodiment, the pharmaceutical composition further comprises a solvent.

In one embodiment, the solvent comprises water.

In one embodiment, the solvent comprises a pharmaceutically acceptable organic solvent. Any of the pharmaceutically acceptable organic solvents described herein can be used in the compositions of the invention.

In one embodiment, the pharmaceutical composition is a solution of the salt in the pharmaceutically acceptable organic solvent.

In one embodiment, the pharmaceutical composition comprises a pharmaceutically acceptable organic solvent and further comprises a phospholipid, a sphingomyelin, or phosphatidyl choline. Without wishing to be bound by theory, it is believed that the phospholipid, sphingomyelin, or phosphatidyl choline facilitates formation of a precipitate when the pharmaceutical composition is injected into water and can also facilitate controlled release of the aptamer from the resulting precipitate. Typically, the phospholipid, sphingomyelin, or phosphatidyl choline is present in an amount ranging from greater than 0 to 10 percent by weight of the pharmaceutical composition. In one embodiment, the phospholipid, sphingomyelin, or phosphatidyl choline is present in an amount ranging from about 0.1 to 10 percent by weight of the pharmaceutical composition. In one embodiment, the phospholipid, sphingomyelin, or phosphatidyl choline is present in an amount ranging from about 1 to 7.5 percent by weight of the pharmaceutical composition. In one embodiment, the phospholipid, sphingomyelin, or phosphatidyl choline is present in an amount ranging from about 1.5 to 5 percent by weight of the pharmaceutical composition. In one embodiment, the phospholipid, sphingomyelin, or phosphatidyl choline is present in an amount ranging from about 2 to 4 percent by weight of the pharmaceutical composition.

The molar ratio of acidic groups on the aptamer to basic groups on the a pharmaceutically acceptable organic base typically ranges from about 2:1 to 1:2. In one embodiment, the molar ratio of acidic groups on the aptamer to basic groups on the pharmaceutically acceptable organic base ranges about 1.5:1 to 1:1.5. In one embodiment, the molar ratio of acidic groups on the aptamer to basic groups on the pharmaceutically acceptable organic base ranges about 1.25:1 to 1:1.25. In one embodiment, the molar ratio of acidic groups on the aptamer to basic groups on the pharmaceutically acceptable organic base ranges about 1.1:1. to 1:1.1. In one embodiment, the molar ratio of acidic groups on the aptamer to basic groups on the pharmaceutically acceptable organic base is about 1:1. A wider range for the molar ratio of acidic groups on the aptamer to basic groups on the pharmaceutically acceptable organic base, however, is also possible. For example, the molar ratio of acidic groups on the aptamer to basic groups on the pharmaceutically acceptable organic base can range from about 15:1 to 1:15.

8.4.1 (i) Pharmaceutical Compositions Comprising
(i) an Amino Acid Ester or Amino Acid Amide and
(ii) a Protonated Aptamer Without wishing to be bound by theory, it is believed that the acidic phosphate groups of the protonated aptamer protonate the amine group of the amino acid ester or amide to form a salt between one or more amino acid ester or amide molecules and the aptamer as illustrated schematically below for an amino acid ester and an aptamer:

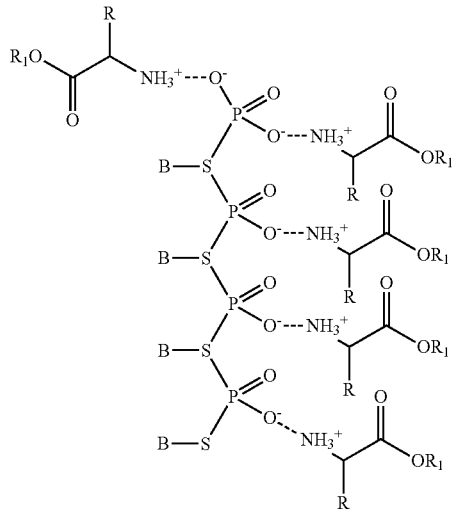

wherein B, S, R, and R$_1$ have the meaning described above. It is not necessary, however, that every phosphate group be ionically bound to an amino acid ester or amino acid amide.

Any amino acid or amino acid ester described above can be used in the pharmaceutical compositions.

Any aptamer described above can be used in the pharmaceutical compositions.

In one embodiment, the pharmaceutical composition further comprises a solvent.

In one embodiment, the solvent comprises water.

In one embodiment, the solvent comprises a pharmaceutically acceptable organic solvent. Any of the pharmaceutically acceptable organic solvents described herein can be used in the compositions of the invention.

In one embodiment, the pharmaceutical composition comprises a pharmaceutically acceptable organic solvent and further comprises a phospholipid, a sphingomyelin, or phosphatidyl choline. Without wishing to be bound by theory, it is believed that the phospholipid, sphingomyelin, or phosphatidyl choline facilitates formation of a precipitate when the pharmaceutical composition is injected into water and can also facilitate controlled release of the aptamer from the resulting precipitate. Typically, the phospholipid, sphingomyelin, or phosphatidyl choline is present in an amount ranging from greater than 0 to 10 percent by weight of the pharmaceutical composition. In one embodiment, the phospholipid, sphingomyelin, or phosphatidyl choline is present in an amount ranging from about 0.1 to 10 percent by weight of the pharmaceutical composition. In one embodiment, the phospholipid, sphingomyelin, or phosphatidyl choline is present in an amount ranging from about 1 to 7.5 percent by weight of the pharmaceutical composition. In one embodiment, the phospholipid, sphingomyelin, or phosphatidyl choline is present in an amount ranging from about 1.5 to 5 percent by weight of the pharmaceutical composition. In one embodiment, the phospholipid, sphingomyelin, or phosphatidyl choline is present in an amount ranging from about 2 to 4 percent by weight of the pharmaceutical composition.

The molar ratio of acidic groups on the aptamer to basic groups on the amino acid ester or amino acid amide typically ranges from about 2:1 to 1:2. In one embodiment, the molar ratio of acidic groups on the aptamer to basic groups on the amino acid ester or amino acid amide ranges from about 1.5:1 to 1:1.5. In one embodiment, the molar ratio of acidic groups on the aptamer to basic groups on the amino acid ester or amino acid amide ranges from about 1.25:1 to 1:1.25. In one embodiment, the molar ratio of acidic groups on the aptamer to basic groups on the amino acid ester or amino acid amide ranges from about 1.1:1. to 1:1.1. In one embodiment, the molar ratio of acidic groups on the aptamer to basic groups on the amino acid ester or amino acid amide is about 1:1. A wider range for the molar ratio of acidic groups on the aptamer to basic groups on the amino acid ester or amino acid, however, is also possible. For example, the molar ratio of acidic groups on the aptamer to basic groups on the amino acid ester or amino acid can range from about 15:1 to 1:15.

8.4.1 (i)(a) Pharmaceutical Compositions wherein the Amino Acid Ester or Amide is an Amino Acid Ester or Amide of Lysine In one embodiment, the pharmaceutical composition comprises an ester or amide of lysine.

In one embodiment, there is less than a molar equivalent of lysine molecules relative to acidic phosphate groups on the aptamer, i.e., there is an excess of acidic phosphate groups on the aptamer relative to amino acid ester or amide molecules.

Without wishing to be bound by theory it is believed that the amino acid ester or amide of lysine cross-links two protonated aptamer molecules as depicted below:

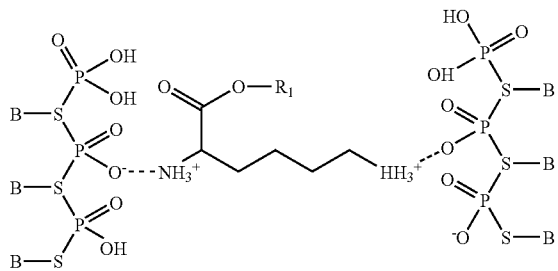

wherein B, S, and $R_1$ have the meaning described above.

Pharmaceutical Compositions Comprising an Ester or Amide of Lysine, a Protonated Aptamer, and a Carboxylic Acid In one embodiment, the amino acid ester or amide is an ester or amide of lysine and the pharmaceutical composition further comprises a carboxylic acid. Without wishing to be bound by theory, it is believed that the carboxylic acid protonates the ε-amine group of lysine to provide a structure as depicted below:

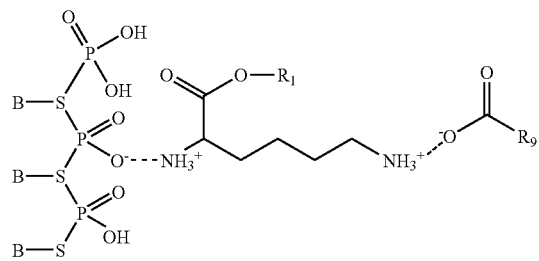

wherein B, S, and $R_1$ are defined above and $R_9$ is a $C_1$-$C_{21}$ hydrocarbon.

The combined molar ratio of acidic groups on the aptamer and acid groups on the carboxylic acid to basic groups on the amino acid ester or amino acid amide typically ranges from about 2:1 to 1:2. In one embodiment, the combined molar ratio of acidic groups on the aptamer and acid groups on the carboxylic acid to basic groups on the amino acid ester or amino acid amide ranges from about 1.5:1 to 1:1.5. In one embodiment, the combined molar ratio of acidic groups on the aptamer and acid groups on the carboxylic acid to basic groups on the amino acid ester or amino acid amide ranges from about 1.25:1 to 1:1.25. In one embodiment, the combined molar ratio of acidic groups on the aptamer and acid groups on the carboxylic acid to basic groups on the amino acid ester or amino acid amide ranges from about 1.1:1. to 1:1.1. In one embodiment, the combined molar ratio of acidic groups on the aptamer and acid groups on the carboxylic acid to basic groups on the amino acid ester or amino acid amide is about 1:1. A wider range for the molar ratio of acidic groups on the aptamer and acid groups on the carboxylic acid to basic groups on the amino acid ester or amino acid amide, however, is also possible. For example, the molar ratio of acidic groups on the aptamer and acid groups on the carboxylic acid to basic groups on the amino acid ester or amino acid amide can range from about 15:1 to 1:15.

Generally, the molar ratio of acidic groups on the aptamer to acid groups on the carboxylic acid ranges from about 20:1 to 1:20. In one embodiment, the molar ratio of acidic groups on the aptamer to acid groups on the carboxylic acid ranges from about 15:1 to 1:15. In one embodiment, the molar ratio of acidic groups on the aptamer to acid groups on the carboxylic acid ranges from about 10:1 to 1:10. In one embodiment, the molar ratio of acidic groups on the aptamer to acid groups on the carboxylic acid ranges from about 5:1 to 1:5. In one embodiment, the molar ratio of acidic groups on the aptamer to acid groups on the carboxylic acid ranges from about 2:1 to 1:2.

The Carboxylic Acid

The carboxylic acid can be any pharmaceutically acceptable carboxylic acid. Typically, the carboxylic acid is a $C_1$-$C_{22}$ carboxylic acid. Suitable carboxylic acids include, but are not limited to, acetic acid, propanoic acid, butanoic acid, pentanoic acid, decanoic acid, hexanoic acid, benzoic acid, caproic acid, lauric acid, myristic acid, palmitic acid, stearic acid, palmic acid, oleic acid, linoleic acid, and linolenic acid.

In one embodiment, the carboxylic acid is a $C_1$-$C_{16}$ carboxylic acid.

In one embodiment, the carboxylic acid is a $C_1$-$C_{10}$ carboxylic acid.

In one embodiment, the carboxylic acid is a $C_1$-$C_5$ carboxylic acid.

In one embodiment, the carboxylic acid is a $C_1$-$C_3$ carboxylic acid.

In one embodiment, the carboxylic acid is a $C_6$-$C_{22}$ carboxylic acid.

In one embodiment, the carboxylic acid is a $C_6$-$C_{18}$ carboxylic acid.

In one embodiment, the carboxylic acid is a $C_8$-$C_{18}$ carboxylic acid.

In one embodiment, the carboxylic acid is a $C_{10}$-$C_{18}$ carboxylic acid.

In one embodiment, the carboxylic acid is a $C_6$-$C_{18}$ carboxylic acid.

In one embodiment, the carboxylic acid is a $C_{16}$-$C_{22}$ carboxylic acid.

In one embodiment, the carboxylic acid is a saturated or unsaturated fatty acid.

In one embodiment, the carboxylic acid is a saturated fatty acid.

In one embodiment, the carboxylic acid is an unsaturated fatty acid.

In one embodiment, the carboxylic acid is a dicarboxylic acid. Suitable dicarboxylic acids include, but are not limited to, oxalic acid, malonic aid, succinic acid, glutamic acid, adipic acid, and pimelic acid.

In one embodiment, the carboxylic acid is a polycarboxylic acid.

The carboxylic acids are commercially available or can be prepared by methods well known to those skilled in the art.

In one embodiment, the carboxylic acid is an N-acyl amino acid. The N-acyl amino acids have the following general formula (III):

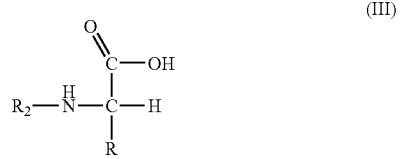

wherein:

R is the amino acid side chain and is defined above; and $R_2$ is an acyl group of formula —C(O)—$R_5$, wherein $R_5$ is a substituted $C_1$ to $C_{21}$ hydrocarbon group, i.e., the acyl group, $R_2$, is a $C_1$- to $C_{22}$ acyl group. Representative acyl groups of formula —C(O)—$R_5$ include, but are not limited to, acetyl, propionyl, butanoyl, hexanoyl, caproyl, heptoyl, octoyl, nonoyl, decoyl, undecoyl, dodecoyl, tridecoyl, tetradecoyl, pentadecoyl, hexadecoyl, heptadecoyl, octadecoyl, laurolyl, myristoyl, palmitoyl, stearoyl, palmioleoyl, oleoyl, linoleoyl, linolenoyl, and benzoyl.

In one embodiment, $R_5$ is a $C_1$-$C_{15}$ hydrocarbon group, i.e., the acyl group of formula —C(O)—$R_5$ is a $C_2$-$C_{16}$ acyl group.

In one embodiment, $R_5$ is a $C_1$-$C_9$ hydrocarbon group, i.e., the acyl group of formula —C(O)—$R_5$ is a $C_2$-$C_{10}$ acyl group.

In one embodiment, $R_5$ is a $C_1$-$C_5$ hydrocarbon group, i.e., the acyl group of formula —C(O)—$R_5$ is a $C_2$-$C_6$ acyl group.

In one embodiment, $R_5$ is a $C_1$-$C_3$ hydrocarbon group, i.e., the acyl group of formula —C(O)—$R_5$ is a $C_2$-$C_4$ acyl group.

In one embodiment, $R_5$ is a $C_5$-$C_{21}$ hydrocarbon group, i.e., the acyl group of formula —C(O)—$R_5$ is a $C_6$-$C_{22}$ acyl group.

In one embodiment, $R_5$ is a $C_5$-$C_{17}$ hydrocarbon group, i.e., the acyl group of formula —C(O)—$R_5$ is a $C_6$-$C_{18}$ acyl group.

In one embodiment, $R_5$ is a $C_7$-$C_{17}$ hydrocarbon group, i.e., the acyl group of formula —C(O)—$R_5$ is a $C_8$-$C_{18}$ acyl group.

In one embodiment, $R_5$ is a $C_9$-$C_{17}$ hydrocarbon group, i.e., the acyl group of formula —C(O)—$R_5$ is a $C_{10}$-$C_{18}$ acyl group.

In one embodiment, $R_5$ is a $C_{15}$-$C_{21}$ hydrocarbon group, i.e., the acyl group of formula —C(O)—$R_5$ is a $C_{16}$-$C_{22}$ acyl group.

In one embodiment, the acyl group of formula —C(O)—$R_5$ is obtained from a saturated or unsaturated fatty acid.

In one embodiment, the acyl group of formula —C(O)—$R_5$ is a caproyl, laurolyl, myristoyl, palmitoyl, stearoyl, palmioleoyl, oleoyl, linoleoyl, or linolenoyl group.

The N-acylated amino acids can be obtained by methods well known to those skilled in the art. For example, the N-acylated amino acids can be obtained by reacting an amino acid with an acid halide of formula T-C(O)—$R_5$, wherein T is a halide, preferably chloride, and $R_1$ is as defined above, using methods well known to those skilled in the art. When N-acylating the amino acid with the acid halide of formula T-C(O)—$R_5$, it may be necessary to protect some other functional group of the amino acid or the acid halide with a protecting group that is subsequently removed after the acylation reaction. One of ordinary skill in the art would readily know what functional groups would need to be protected before acylating the amino acid with the acid halide of formula T-C(O)—$R_5$. Suitable protecting groups are known to those skilled in the art such as those described in T. W. Greene, et al. *Protective Groups in Organic Synthesis*, $3^{rd}$ ed. (1999).

Acid halides can be obtained using methods well known to those skilled in the art such as those described in J. March, *Advanced Organic Chemistry, Reaction Mechanisms and Structure*, $4^{th}$ ed. John Wiley & Sons, N.Y., 1992, pp. 437-8. For example, acid halides can be prepared by reacting a carboxylic acid with thionyl chloride, bromide, or iodide. Acid chlorides and bromides can also be prepared by reacting a carboxylic acid with phosphorous trichloride or phosphorous tribromide, respectively. Acid chlorides can also be prepared by reacting a carboxylic acid with $Ph_3P$ in carbon tetrachloride. Acid fluorides can be prepared by reacting a carboxylic acid with cyanuric fluoride.

As discussed later, by varying the structure of carboxylic acid it is possible to vary the properties of the pharmaceutical compositions.

Pharmaceutical Compositions Comprising an Ester or Amide of Lysine, a Protonated Aptamer, and a Phospholipid, Phosphatidyl Choline, or a Sphingomyelin In another embodiment, the amino acid ester or amide is an ester or amide of lysine and the pharmaceutical composition further comprises a phospholipid, phosphatidyl choline, or a sphingomyelin. Without wishing to be bound by theory, it is believed that protonated phosphate groups on the phospholipid, phosphatidyl choline, or sphingomyelin protonates the ε-amine group of lysine to provide a structure as depicted below for a phospholipid:

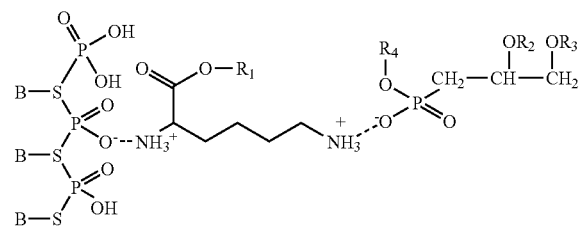

wherein B, S, $R_1$, $R_2$, $R_3$, and $R_4$ are defined above.

The combined molar ratio of acidic groups on the aptamer and acidic groups on the phospholipid, phosphatidyl choline, or sphingomyelin to basic groups on the amino acid ester or amino acid amide typically ranges from about 2:1 to 1:2. In one embodiment, the combined molar ratio of acidic groups on the aptamer and acidic groups on the phospholipid, phosphatidyl choline, or sphingomyelin to basic groups on the amino acid ester or amino acid amide ranges from about 1.5:1 to 1:1.5. In one embodiment, the combined molar ratio of acidic groups on the aptamer and acidic groups on the phospholipid, phosphatidyl choline, or sphingomyelin to basic groups on the amino acid ester or amino acid amide ranges from about 1.25:1 to 1:1.25. In one embodiment, the combined molar ratio of acidic groups on the aptamer and acidic groups on the phospholipid, phosphatidyl choline, or sphingomyelin to basic groups on the amino acid ester or amino acid amide ranges from about 1.1:1. to 1:1.1. In one embodiment, the combined molar ratio of acidic groups on the aptamer and acidic groups on the phospholipid, phosphatidyl choline, or sphingomyelin to basic groups on the amino acid ester or amino acid amide is about 1:1. A wider range for the molar ratio of acidic groups on the aptamer and acidic groups on the phospholipid, phosphatidyl choline, or sphingomyelin to basic groups on the amino acid ester or amino acid amide, however, is also possible. For example, the molar ratio of acidic groups on the aptamer and acidic groups on the phospholipid, phosphatidyl choline, or sphingomyelin to basic groups on the amino acid ester or amino acid amide can range from about 15:1 to 1:15.

Generally, the molar ratio of acidic groups on the aptamer to acidic groups on the phospholipid, phosphatidyl choline, or sphingomyelin ranges from about 20:1 to 1:20. In one embodiment, the molar ratio of acidic groups on the aptamer to acidic groups on the phospholipid, phosphatidyl choline, or sphingomyelin ranges from about 15:1 to 1:15. In one embodiment, the molar ratio of acidic groups on the aptamer to acidic groups on the phospholipid, phosphatidyl choline, or sphingomyelin ranges from about 10:1 to 1:10. In one embodiment, the molar ratio of acidic groups on the aptamer to acidic groups on the phospholipid, phosphatidyl choline, or sphingomyelin ranges from about 5:1 to 1:5. In one embodiment, the molar ratio of acidic groups on the aptamer to acidic groups on the phospholipid, phosphatidyl choline, or sphingomyelin ranges from about 2:1 to 1:2.

As discussed later, by varying the structure of phospholipid, phosphatidyl choline, or sphingomyelin it is possible to vary the properties of the pharmaceutical compositions.

The Phospholipid

Any pharmaceutically acceptable phospholipid can be used in the pharmaceutical compositions of the invention.

Representative, pharmaceutically acceptable phospholipids include, but are not limited to:

phosphatidic acids of general formula:

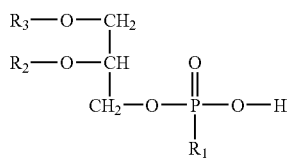

wherein $R_1$, $R_2$, and $R_3$ are defined above. Suitable phosphatidic acids suitable for use in the compositions and methods of the invention include, but are not limited to, the 1-acyl-2-acyl-sn-glycero-3-phosphates and the 1,2-diacyl-sn-glycero-3-phosphates commercially available from Avanti Polar Lipids Inc. of Alabaster, Ala.

phosphatidylethanolamines of general formula

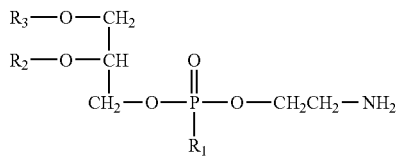

wherein $R_1$, $R_2$, and $R_3$ are defined above. Suitable phosphatidylethanolamines suitable for use in the compositions and methods of the invention include, but are not limited to, the 1-acyl-2-acyl-sn-glycero-3-phosphoethanolamines and the 1,2-diacyl-sn-glycero-3-phosphoethanolamines commercially available from Avanti Polar Lipids Inc. of Alabaster, Ala.

phosphatidylcholines of general formula

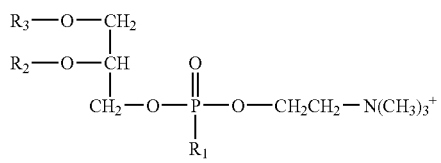

wherein $R_1$, $R_2$, and $R_3$ are defined above. Suitable phosphatidylcholines suitable for use in the compositions and methods of the invention include, but are not limited to, the 1-acyl-2-acyl-sn-glycero-3-phosphocholines, the 1,2-diacyl-sn-glycero-3-phosphoethanolamines (saturated series), and the 1,2-diacyl-sn-glycero-3-phosphoethanolamines (unsaturated series), commercially available from Avanti Polar Lipids Inc. of Alabaster, Ala. and Phospholipon®—50PG, Phospholipon®—53MCT, Phospholipon®—75SA, Phospholipon®—80, Phospholipon®—90NG, Phospholipon®—90H, and Phospholipon®—100H, commercially available from Phospholipid GmbH of Cologne, Germany. In one embodiment, the phospholipid is Phospholipon®—90H.

phosphatidylserines of general formula

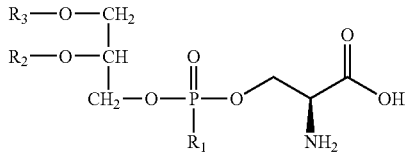

wherein $R_1$, $R_2$, and $R_3$ are defined above. Suitable phosphatidylserines suitable for use in the compositions and methods of the invention include, but are not limited to, the 1-acyl-2-acyl-sn-glycero-3-[phospho-L-serine]s and the 1,2-diacyl-sn-glycero-3-[phospho-L-serine]s commercially available from Avanti Polar Lipids Inc. of Alabaster, Ala.

plasmalogens of general formula

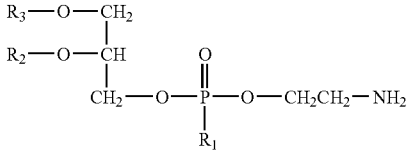

wherein $R_1$ and $R_2$ are defined above and $R_3$ is —C=C—$R_9$, wherein $R_9$ is defined above. Suitable plasmalogens suitable for use in the compositions and methods of the invention include, but are not limited to, C16(Plasm)-12:0 NBD PC, C16(Plasm)-18:1 PC, C16(Plasm)-20:4 PC, C16(Plasm)-22:6 PC, C16(Plasm)-18:1 PC, C16(Plasm)-20:4 PE, and C16(Plasm)-22:6 PE, commercially available from Avanti Polar Lipids Inc. of Alabaster, Ala.

phosphatidylglycerols of general formula

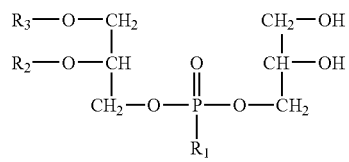

wherein $R_1$, $R_2$, and $R_3$ are defined above. Suitable phosphatidylglycerols suitable for use in the compositions and methods of the invention include, but are not limited to, the 1-acyl-2-acyl-sn-glycero-3-[phospho-rac-(1-glycerol)]s and the 1,2-diacyl-sn-glycero-3-[phospho-rac-(1-glycerol)]s, commercially available from Avanti Polar Lipids Inc. of Alabaster, Ala.

phosphatidylinositols of general formula

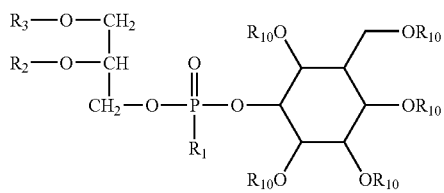

wherein $R_1$, $R_2$, $R_3$, and $R_{10}$ are defined above. Suitable phosphatidylinositols suitable for use in the compositions and methods of the invention include, but are not limited to, phosphatidylinositol, phosphatidylinositol-4-phosphate, and phosphatidylinositol-4,5-bisphosphate, commercially available from Avanti Polar Lipids Inc. of Alabaster, Ala.

The phospholipids are commercially available or can be obtained by methods well known to those skilled in the art. Representative methods for obtaining phospholipids are described in Sandra Pesch et al., *Properties of Unusual Phospholipids Bearing Acetylenic Fatty Acids*, Tettrahedron, vol. 15, no. 43, 14,627-14634 (1997); Sepp D. Kohlwein, *Phospholipid Synthesis, Sorting, Subcellular Traffic—The Yeast Approach*, Trends in Cell Biology, vol. 6, 260-266 (1996), Serguei V. Vinogradov, *Synthesis of Phospholipids—Oligodeoxyribonucleotide Conjugates*, Tett. Lett., vol. 36, no. 14, 2493-2496 (1995), and references cited therein.

In one embodiment, the phospholipid is Phospholipon®—E:80 (commercially from Phospholipid GmbH of Cologne, Germany or American Lecithin Company of Oxford Conn.).

In one embodiment, the phospholipid is Phospholipon®—80G (commercially available from Phospholipid GmbH of Cologne, Germany or American Lecithin Company of Oxford Conn.).

In one embodiment, the phospholipid is Phospholipon®—85G (commercially available from Phospholipid GmbH of Cologne, Germany or American Lecithin Company of Oxford Conn.).

In one embodiment, the phospholipid is Phospholipon®—100H (commercially available from Phospholipid GmbH of Cologne, Germany or American Lecithin Company of Oxford Conn.).

The Sphingomyelin

Any pharmaceutically acceptable sphingomyelin can be used in the pharmaceutical compositions of the invention.

In one embodiment, the sphingomyelin is

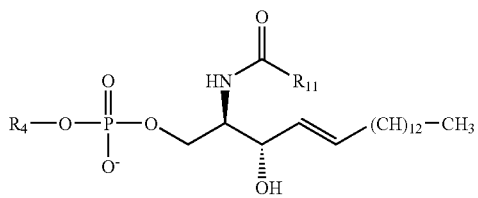

wherein $R_{11}$ is a $C_1$-$C_{24}$ linear, saturated or unsaturated hydrocarbon and $R_4$ is —$CH_2CH_2N(CH_3)_3^+$. In another embodiment, $R_{11}$ is a $C_8$-$C_{24}$ linear, saturated or unsaturated hydrocarbon and $R_4$ is —$CH_2CH_2N(CH_3)_3^+$. In another embodiment, $R_{11}$ is a $C_{16}$-$C_{24}$ linear, saturated or unsaturated hydrocarbon and $R_4$ is —$CH_2CH_2N(CH_3)_3^+$.

Suitable sphingomyelins include, but are not limited to, C2-Sphingomyelin, C6-Sphingomyelin, C18-Sphingomyelin, C6-NBD-Sphingomyelin, and C12-NBD Sphingomyelin, commercially available from Avanti Polar Lipids Inc. of Alabaster, Ala.

Similarly, in another embodiment, the amino acid ester or amide is an ester or amide of lysine and the pharmaceutical composition further comprises a phosphatidyl choline. Without wishing to be bound by theory, it is believed that protonated phosphate groups on the phosphatidyl choline protonates the ε-amine group of lysine to provide a structure as depicted below:

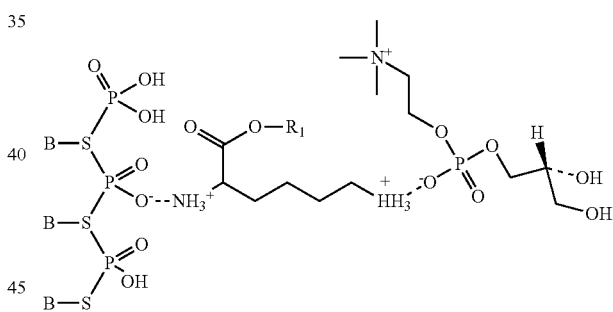

wherein S, B, and $R_1$ are defined above.

Without wishing to be bound by theory it is also believed that pharmaceutical compositions that comprise an amino acid ester or amide of lysine and further comprise a phospholipid, phosphatidyl choline, or a sphingomyelin that the ester or amide of lysine also forms structures wherein each amino group of the lysine ester or amide is protonated by a phospholipid, phosphatidyl choline, or sphingomyelin molecule. Such a structure is depicted below for a phospholipid:

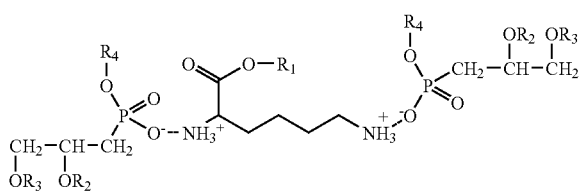

wherein $R_1$, $R_2$, $R_3$, and $R_4$ are defined above.

The invention also includes pharmaceutical compositions such as those described above that include an ester or amide of lysine, wherein the ester or amide of lysine is replaced with another diamine such as, for example N,N'-dibenzylethylenediamine.

8.4.1 (i)(b) Pharmaceutical Compositions Comprising a Diester or Diamide of Aspartic Acid or Glutamic Acid and a Protonated Aptamer In another embodiment, the amino acid ester or amide is an ester or amide of aspartic acid or glutamic acid and the side chain carboxylic acid group of the aspartic acid or glutamic acid is also esterified or amidated, i.e., a diester or diamide of aspartic acid or glutamic acid. Without wishing to be bound by theory it is believed that the acidic phosphate groups of the aptamer protonate the amine group of the diester or diamide of aspartic acid or glutamic acid to form a salt between diester or diamide of aspartic acid or glutamic acid and the aptamer as illustrated below for a diester of aspartic acid that is protonated by an aptamer to provide a structure as depicted below:

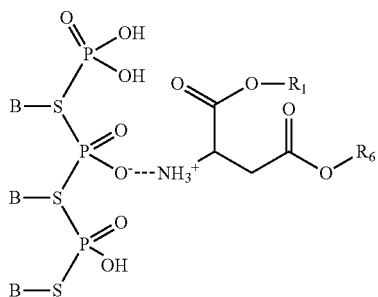

wherein S, B, and $R_1$ are defined above and $R_6$ is defined below.

The diesters of aspartic acid and glutamic acid have the structures:

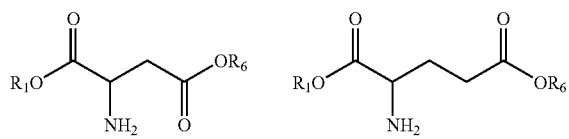

respectively, wherein $R_1$ is defined above and $R_6$ is the same as $R_1$. $R_1$ and $R_6$ can be the same or different. Typically, however, $R_1$ and $R_6$ are the same.

The diamides of aspartic acid and glutamic acid have the structures:

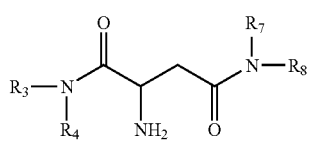

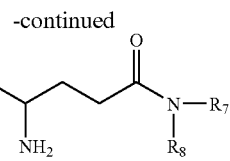

respectively, wherein $R_3$ and $R_4$ are defined above, $R_7$ is the same as $R_3$, and $R_8$ is the same as $R_4$. The amide groups —N($R_3$)($R_4$) and —N($R_7$)($R_8$) can be the same or different. Typically, however, the amide groups —N($R_3$)($R_4$) and —N($R_7$)($R_8$) are the same.

The molar ratio of acidic groups on the aptamer to the diester or diamide of aspartic acid or glutamic acid typically ranges from about 2:1 to 1:2. In one embodiment, the molar ratio of acidic groups on the aptamer to the diester or diamide of aspartic acid or glutamic acid ranges from about 1.5:1 to 1:1.5. In one embodiment, the molar ratio of acidic groups on the aptamer to the diester or diamide of aspartic acid or glutamic acid ranges from about 1.25:1 to 1:1.25. In one embodiment, the molar ratio of acidic groups on the aptamer to the diester or diamide of aspartic acid or glutamic acid ranges from about 1.1:1. to 1:1.1. In one embodiment, the molar ratio of acidic groups on the aptamer to the diester or diamide of aspartic acid or glutamic acid is about 1:1. A wider range for molar ratio of acidic groups on the aptamer to the diester or diamide of aspartic acid or glutamic acid, however, is also possible. For example, the molar ratio of acidic groups on the aptamer to the diester or diamide of aspartic acid or glutamic acid can range from about 15:1 to 1:15.

As discussed later, by varying the structure of diester or diamide of aspartic acid or glutamic acid, i.e., $R_1$ and $R_6$ of the diester and $R_3$, $R_4$, $R_7$, and $R_8$ of the diamide, it is possible to vary the properties of the pharmaceutical compositions.

8.4.1 (ii) Pharmaceutical Compositions Comprising (i) a Protonated Aptamer, and (ii) a Polylysine In another embodiment, the pharmaceutical compositions comprise a protonated aptamer and polylysine.

Any of the aptamers described above can be used in the pharmaceutical compositions.

Any polylysine (for example, any of the polylysines commercially available from Sigma-Aldrich of Milwaukee, Wis. as the hydrobromide salt, which can be converted to polylysine as described later) can be used in the pharmaceutical compositions. In one embodiment, the polylysine has a molecular weight range of from about 1,000 to 4,000. In one embodiment, the polylysine has a molecular weight range of from about 4,000 to 15,000. In one embodiment, the polylysine has a molecular weight range of from about 15,000 to 30,000. In one embodiment, the polylysine has a molecular weight range of from about 30,000 to 70,000. In one embodiment, the polylysine has a molecular weight range of from about 70,000 to 150,000. In one embodiment, the polylysine has a molecular weight range of from about 150,000 to 300,000.

Without wishing to be bound by theory, it is believed that the amine groups on the polylysine are protonated by acidic phosphate groups on the aptamer.

Typically, the amount of polylysine relative to the amount of the aptamer is an amount sufficient to provide a solution of the pharmaceutical composition (for example, a methanol or aqueous solution) having a pH value ranging from about 3 to 10. In one embodiment, a solution of the pharmaceutical composition has a pH value ranging from about 5 to 9. In one embodiment, a solution of the pharmaceutical composition has a pH value ranging from about 6 to 8. In one embodiment, a solution of the pharmaceutical composition has a pH value of about 7. Other pH ranges, however, are also within the scope of the invention. For example, in one embodiment, a solution of the pharmaceutical composition has a pH value ranging from about 3 to 7 and in another embodiment a solution of the pharmaceutical composition has a pH value ranging from about 7 to 10.

The pH can be readily measured by dissolving the pharmaceutical composition in a solvent (for example methanol or water) and removing a few microliters of the resulting solution and applying it to a wet pH test strip (such as commercially available from Sigma-Aldrich of Milwaukee, Wis.) that indicates the pH of the solution by the color of the test strip after the solution is applied.

In one embodiment, the pharmaceutical composition comprising a protonated aptamer and polylysine further comprises a solvent. In one embodiment, the solvent comprises water. In one embodiment, the solvent is water. In one embodiment, the solvent comprises a pharmaceutically acceptable organic solvent. In one embodiment, the solvent is a pharmaceutically acceptable organic solvent. In one embodiment, the solvent comprises N-methyl pyrrolidone. In one embodiment, the solvent is N-methyl pyrrolidone.

Advantageously, the pharmaceutical compositions comprising a protonated aptamer and polylysine have increased solubility in water and organic solvents. For example, the pharmaceutical composition formed between pegylated ARC259 and polylysine having an average molecular weight of about 13,000 is soluble in water and N-methyl pyrrolidone at a concentration of up to about 12% (w/v). In contrast, polylysine having an average molecular weight of about 13,000 (obtained as described later from the commercially available hydrobromide salt) and the protonated aptamer are both essentially insoluble in water and N-methyl pyrrolidone.

8.4.2 Pharmaceutical Compositions Comprising (i) an Aptamer, (ii) a Divalent Metal Cation, and (iii) Optionally a Carboxylate, a Phospholipid, a Phosphatidyl Choline, or a Sphingomyelin In another embodiment, the pharmaceutical compositions comprise (i) an aptamer, (ii) a divalent metal cation and (iii) optionally a carboxylate, a phospholipid, a phosphatidyl choline, or a sphingomyelin. Without wishing to be bound by theory, it is believed that the divalent metal cation interacts with the phosphate groups on the aptamer to form a structure as depicted below:

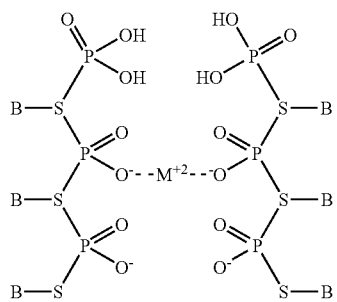

wherein $M^{+2}$ is a divalent metal cation and B and S are defined above.

Without wishing to be bound by theory, it is believed that when the pharmaceutical composition includes the optional carboxylate, phospholipid, phosphatidyl choline, or sphingomyelin the divalent metal cation interacts with the phosphate groups on the aptamer and the carboxylate, phospholipid, phosphatidyl choline, or sphingomyelin to form a structure as depicted below for a carboxylate:

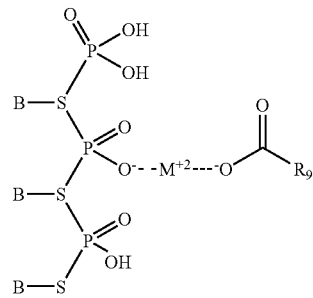

wherein $M^{+2}$, B, S, and $R_9$ are defined above. Without wishing to be bound by theory, it is believed that the structures are similar to the structures formed between an aptamer; the amino acid lysine; and a carboxylic acid, a phospholipid, phosphatidyl choline, or a sphingomyelin, described above, except that the divalent metal cation replaces the lysine.

Without wishing to be bound by theory it is also believed that when the pharmaceutical composition includes the optional carboxylate, phospholipid, phosphatidyl choline, or sphingomyelin the divalent metal cation interacts with more than one carboxylate, phospholipid, phosphatidyl choline, or sphingomyelin to form a structure as depicted below for a carboxylate:

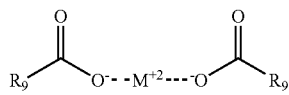

wherein $M^{+2}$ and $R_9$ are defined above.

In one embodiment, the pharmaceutical composition comprises a carboxylate.
In one embodiment, the pharmaceutical composition comprises a phospholipid.
In one embodiment, the pharmaceutical composition comprises phosphatidyl choline.
In one embodiment, the pharmaceutical composition comprises a sphingomyelin.

Any of the aptamers described above can be used in the pharmaceutical compositions.

The carboxylate can be obtained from any pharmaceutically acceptable carboxylic acid. Any of the carboxylic acids described herein can be used to provide the carboxylate.

In one embodiment, the carboxylic acid is an N-acyl amino acid of general formula (III). Any N-acyl amino acid of general formula (III) described above can be used in the pharmaceutical compositions.

Any of the phospholipids described above can be used in the pharmaceutical compositions.

Any of the sphingomyelins described above can be used in the pharmaceutical compositions.

Suitable divalent metal cations include, but are not limited to, the alkaline earth metal cations, $Mg^{+2}$, $Zn^{+2}$, $Cu^{+2}$, and $Fe^{+2}$. Preferred divalent metal cations are $Ca^{+2}$, $Mg^{+2}$, $Zn^{+2}$, $Cu^{+2}$, and $Fe^{+2}$.

The combined molar ratio of anionic groups on the aptamer and anionic groups on the carboxylate, phospholipid, phosphatidyl choline, or sphingomyelin to the divalent metal cation typically ranges from about 4:1 to 1:4. In one embodiment, the combined molar ratio of anionic groups on the aptamer and anionic groups on the carboxylate, phospholipid, phosphatidyl choline, or sphingomyelin to the divalent metal cation ranges from about 3:1 to 1:3. In one embodiment, the combined molar ratio of anionic groups on the aptamer and anionic groups on the carboxylate, phospholipid, phosphatidyl choline, or sphingomyelin to the divalent metal cation ranges from about 2.5:1 to 1:2.5. In one embodiment, the combined molar ratio of anionic groups on the aptamer and anionic groups on the carboxylate, phospholipid, phosphatidyl choline, or sphingomyelin to the divalent metal cation ranges from about 2:1. to 1:2. In one embodiment, the combined molar ratio of anionic groups on the aptamer and anionic groups on the carboxylate, phospholipid, phosphatidyl choline, or sphingomyelin to the divalent metal cation is about 2:1. A wider range for the molar ratio of anionic groups on the aptamer and anionic groups on the carboxylate, phospholipid, phosphatidyl choline, or sphingomyelin to the divalent metal cation, however, is also possible. For example, the molar ratio of anionic groups on the aptamer and anionic groups on the carboxylate, phospholipid, phosphatidyl choline, or sphingomyelin to the divalent metal cation can range from about 15:1 to 1:15.

Generally, the molar ratio of anionic groups on the aptamer to anionic groups on the carboxylate, phospholipid, phosphatidyl choline, or sphingomyelin ranges from about 20:1 to 1:20. In one embodiment, the molar ratio of anionic groups on the aptamer to anionic groups on the carboxylate, phospholipid, phosphatidyl choline, or sphingomyelin ranges from about 15:1 to 1:15. In one embodiment, the molar ratio of anionic groups on the aptamer to anionic groups on the carboxylate, phospholipid, phosphatidyl choline, or sphingomyelin ranges from about 10:1 to 1:10. In one embodiment, the molar ratio of anionic groups on the aptamer to anionic groups on the carboxylate, phospholipid, phosphatidyl choline, or sphingomyelin ranges from about 5:1 to 1:5. In one embodiment, the molar ratio of anionic groups on the aptamer to anionic groups on the carboxylate, phospholipid, phosphatidyl choline, or sphingomyelin ranges from about 2:1 to 1:2.

By varying the structure of the carboxylate, phospholipid, phosphatidyl choline, or sphingomyelin it is possible to vary the properties of the pharmaceutical compositions, as is discussed later.

8.5 Optional Additives

The pharmaceutical compositions can optionally comprise one or more additional excipients or additives to provide a dosage form suitable for administration to an animal. When administered to an animal, the aptamer containing pharmaceutical compositions are typically administered as a component of a composition that comprises a pharmaceutically acceptable carrier or excipient so as to provide the form for proper administration to the animal. Suitable pharmaceutical excipients are described in *Remington's Pharmaceutical Sciences* 1447-1676 (Alfonso R. Gennaro ed., 19th ed. 1995), incorporated herein by reference. The pharmaceutical compositions can take the form of solutions, suspensions, emulsion, tablets, pills, pellets, capsules, capsules containing liquids, powders, suppositories, emulsions, aerosols, sprays, suspensions, or any other form suitable for use.

In one embodiment, the pharmaceutical compositions are formulated for intravenous or parenteral administration. Typically, compositions for intravenous or parenteral administration comprise a suitable sterile solvent, which may be an isotonic aqueous buffer or pharmaceutically acceptable organic solvent. Where necessary, the compositions can also include a solubilizing agent. Compositions for intravenous administration can optionally include a local anesthetic such as lidocaine to lessen pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where aptamer containing pharmaceutical compositions are to be administered by infusion, they can be dispensed, for example, with an infusion bottle containing, for example, sterile pharmaceutical grade water or saline. Where the pharmaceutical compositions are administered by injection, an ampoule of sterile water for injection, saline, or other solvent such as a pharmaceutically acceptable organic solvent can be provided so that the ingredients can be mixed prior to administration.

In another embodiment, the pharmaceutical compositions are formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Oral compositions can include standard excipients such as mannitol, lactose, starch, magnesium stearate, sodium saccharin, cellulose, and magnesium carbonate. Typically, the excipients are of pharmaceutical grade. Orally administered compositions can also contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, when in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. A time-delay material such as glycerol monostearate or glycerol stearate can also be used.

The pharmaceutical compositions further comprising a solvent can optionally comprise a suitable amount of a pharmaceutically acceptable preservative, if desired, so as to provide additional protection against microbial growth. Examples of preservatives useful in the pharmaceutical compositions of the invention include, but are not limited to, potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chlorides (e.g., benzethonium chloride).

In one embodiment, the pharmaceutical compositions of the invention optionally contain a suitable amount of a pharmaceutically acceptable polymer. The polymer can increase the viscosity of the pharmaceutical composition. Suitable polymers for use in the compositions and methods of the invention include, but are not limited to, hydroxypropylcellulose, hydoxypropylmethylcellulose (HPMC), chitosan, polyacrylic acid, and polymethacrylic acid.

Typically, the polymer is present in an amount ranging from greater than 0 to 10 percent by weight of the pharmaceutical composition.

In one embodiment, the polymer is present in an amount ranging from about 0.1 to 10 percent by weight of the pharmaceutical composition.

In one embodiment, the polymer is present in an amount ranging from about 1 to 7.5 percent by weight of the pharmaceutical composition.

In one embodiment, the polymer is present in an amount ranging from about 1.5 to 5 percent by weight of the pharmaceutical composition.

In one embodiment, the polymer is present in an amount ranging from about 2 to 4 percent by weight of the pharmaceutical composition.

In one embodiment, the pharmaceutical compositions of the invention are substantially free of polymers.

In one embodiment, any additional components added to the pharmaceutical compositions of the invention are designated as GRAS by the FDA for use or consumption by animals.

In one embodiment, any additional components added to the pharmaceutical compositions of the invention are designated as GRAS by the FDA for use or consumption by humans.

The components of the pharmaceutical composition (the solvents and any other optional components) are preferably biocompatible and non-toxic and, over time, are simply absorbed and/or metabolized by the body.

8.5.1 Pharmaceutical Compositions Further Comprising a Solvent

As described above, the pharmaceutical compositions of the invention can further comprise a solvent.

In one embodiment, the solvent comprises water.

In one embodiment, the solvent comprises a pharmaceutically acceptable organic solvent.

Typically, aptamers are available as the salt of a metal cation, for example, as the potassium or sodium salt. These salts, however, have low solubility in aqueous solvents and/or organic solvents, typically, less than about 25 mg/mL. The pharmaceutical compositions of the invention comprising (i) an amino acid ester or amino acid amide and (ii) a protonated aptamer, however, are significantly more soluble in aqueous solvents and/or organic solvents. Without wishing to be bound by theory, it is believed that the amino acid ester or amino acid amide and the protonated aptamer form a salt, such as illustrated above, and the salt is soluble in aqueous and/or organic solvents.

Similarly, without wishing to be bound by theory, it is believed that the pharmaceutical compositions comprising (i) an aptamer; (ii) a divalent metal cation; and (iii) optionally a carboxylate, a phospholipid, a phosphatidyl choline, or a sphingomyelin form a salt, such as illustrated above, and the salt is soluble in aqueous and/or organic solvents.

In one embodiment, the concentration of the aptamer in the solvent is greater than about 2 percent by weight of the pharmaceutical composition. In one embodiment, the concentration of the aptamer in the solvent is greater than about 5 percent by weight of the pharmaceutical composition. In one embodiment, the concentration of the aptamer in the solvent is greater than about 7.5 percent by weight of the pharmaceutical composition. In one embodiment, the concentration of the aptamer in the solvent is greater than about 10 percent by weight of the pharmaceutical composition. In one embodiment, the concentration of the aptamer in the solvent is greater than about 12 percent by weight of the pharmaceutical composition. In one embodiment, the concentration of the aptamer in the solvent is greater than about 15 percent by weight of the pharmaceutical composition. In one embodiment, the concentration of the aptamer in the solvent is ranges from about 2 percent to 5 percent by weight of the pharmaceutical composition. In one embodiment, the concentration of the aptamer in the solvent is ranges from about 2 percent to 7.5 percent by weight of the pharmaceutical composition. In one embodiment, the concentration of the aptamer in the solvent ranges from about 2 percent to 10 percent by weight of the pharmaceutical composition. In one embodiment, the concentration of the aptamer in the solvent is ranges from about 2 percent to 12 percent by weight of the pharmaceutical composition. In one embodiment, the concentration of the aptamer in the solvent is ranges from about 2 percent to 15 percent by weight of the pharmaceutical composition. In one embodiment, the concentration of the aptamer in the solvent is ranges from about 2 percent to 20 percent by weight of the pharmaceutical composition.

Any pharmaceutically acceptable organic solvent can be used in the pharmaceutical compositions of the invention. Representative, pharmaceutically acceptable organic solvents include, but are not limited to, pyrrolidone, N-methyl-2-pyrrolidone, polyethylene glycol, propylene glycol (i.e., 1,3-propylene glycol), glycerol formal, isosorbid dimethyl ether, ethanol, dimethyl sulfoxide, tetraglycol, tetrahydrofurfuryl alcohol, triacetin, propylene carbonate, dimethyl acetamide, dimethyl formamide, dimethyl sulfoxide, and combinations thereof.

In one embodiment, the pharmaceutically acceptable organic solvent is a water soluble solvent. A representative pharmaceutically acceptable water soluble organic solvents is triacetin.

In one embodiment, the pharmaceutically acceptable organic solvent is a water miscible solvent. Representative pharmaceutically acceptable water miscible organic solvents include, but are not limited to, glycerol formal, polyethylene glycol, and propylene glycol.

In one embodiment, the pharmaceutically acceptable organic solvent comprises pyrrolidone. In one embodiment, the pharmaceutically acceptable organic solvent is pyrrolidone substantially free of another organic solvent.

In one embodiment, the pharmaceutically acceptable organic solvent comprises N-methyl-2-pyrrolidone. In one embodiment, the pharmaceutically acceptable organic solvent is N-methyl-2-pyrrolidone substantially free of another organic solvent.

In one embodiment, the pharmaceutically acceptable organic solvent comprises polyethylene glycol. In one embodiment, the pharmaceutically acceptable organic solvent is polyethylene glycol substantially free of another organic solvent.

In one embodiment, the pharmaceutically acceptable organic solvent comprises propylene glycol. In one embodiment, the pharmaceutically acceptable organic solvent is propylene glycol substantially free of another organic solvent.

In one embodiment, the pharmaceutically acceptable organic solvent comprises glycerol formal. In one embodiment, the pharmaceutically acceptable organic solvent is glycerol formal substantially free of another organic solvent.

In one embodiment, the pharmaceutically acceptable organic solvent comprises isosorbid dimethyl ether. In one embodiment, the pharmaceutically acceptable organic solvent is isosorbid dimethyl ether substantially free of another organic solvent.

In one embodiment, the pharmaceutically acceptable organic solvent comprises ethanol. In one embodiment, the pharmaceutically acceptable organic solvent is ethanol substantially free of another organic solvent.

In one embodiment, the pharmaceutically acceptable organic solvent comprises dimethyl sulfoxide. In one embodiment, the pharmaceutically acceptable organic solvent is dimethyl sulfoxide substantially free of another organic solvent.

In one embodiment, the pharmaceutically acceptable organic solvent comprises tetraglycol. In one embodiment, the pharmaceutically acceptable organic solvent is tetraglycol substantially free of another organic solvent.

In one embodiment, the pharmaceutically acceptable organic solvent comprises tetrahydrofurfuryl alcohol. In one embodiment, the pharmaceutically acceptable organic solvent is tetrahydrofurfuryl alcohol substantially free of another organic solvent.

In one embodiment, the pharmaceutically acceptable organic solvent comprises triacetin. In one embodiment, the pharmaceutically acceptable organic solvent is triacetin substantially free of another organic solvent.

In one embodiment, the pharmaceutically acceptable organic solvent comprises propylene carbonate. In one embodiment, the pharmaceutically acceptable organic solvent is propylene carbonate substantially free of another organic solvent.

In one embodiment, the pharmaceutically acceptable organic solvent comprises dimethyl acetamide. In one embodiment, the pharmaceutically acceptable organic solvent is dimethyl acetamide substantially free of another organic solvent.

In one embodiment, the pharmaceutically acceptable organic solvent comprises dimethyl formamide. In one embodiment, the pharmaceutically acceptable organic solvent is dimethyl formamide substantially free of another organic solvent.

In one embodiment, the pharmaceutically acceptable organic solvent comprises at least two pharmaceutically acceptable organic solvents.

In one embodiment, the pharmaceutically acceptable organic solvent comprises N-methyl-2-pyrrolidone and glycerol formal. In one embodiment, the pharmaceutically acceptable organic solvent is N-methyl-2-pyrrolidone and glycerol formal. In one embodiment, the ratio of N-methyl-2-pyrrolidone to glycerol formal ranges from about 90:10 to 10:90.

In one embodiment, the pharmaceutically acceptable organic solvent comprises propylene glycol and glycerol formal. In one embodiment, the pharmaceutically acceptable organic solvent is propylene glycol and glycerol formal. In one embodiment, the ratio of propylene glycol to glycerol formal ranges from about 90:10 to 10:90.

In one embodiment, the pharmaceutically acceptable organic solvent is a solvent that is recognized as GRAS by the FDA for administration or consumption by animals.

In one embodiment, the pharmaceutically acceptable organic solvent is a solvent that is recognized as GRAS by the FDA for administration or consumption by humans.

In one embodiment, the pharmaceutically acceptable organic solvent is substantially free of water. In one embodiment, the pharmaceutically acceptable organic solvent contains less than about 1 percent by weight of water. In one embodiment, the pharmaceutically acceptable organic solvent contains less about 0.5 percent by weight of water. In one embodiment, the pharmaceutically acceptable organic solvent contains less about 0.2 percent by weight of water. Pharmaceutically acceptable organic solvents that are substantially free of water are advantageous since they are not conducive to bacterial growth. Accordingly, it is typically not necessary to include a preservative in pharmaceutical compositions that are substantially free of water. Another advantage of pharmaceutical compositions that use a pharmaceutically acceptable organic solvent, preferably substantially free of water, is that the solvent is that hydrolysis of the aptamer is minimized. Typically, the more water present in the solvent the more readily the aptamer can be hydrolyzed. Accordingly, aptamer containing pharmaceutical compositions that use a pharmaceutically acceptable organic solvent as the solvent can be more stable than aptamer containing pharmaceutical compositions that use water as the solvent.

In one embodiment, comprising a pharmaceutically acceptable organic solvent, the pharmaceutical composition is injectable.

In one embodiment, the injectable pharmaceutical compositions are of sufficiently low viscosity that they can be easily drawn into a 20 gauge and needle and then easily expelled from the 20 gauge needle. Typically, the viscosity of the injectable pharmaceutical compositions are less than about 1,200 cps. In one embodiment, the viscosity of the injectable pharmaceutical compositions are less than about 1,000 cps. In one embodiment, the viscosity of the injectable pharmaceutical compositions are less than about 800 cps. In one embodiment, the viscosity of the injectable pharmaceutical compositions are less than about 500 cps. Injectable pharmaceutical compositions having a viscosity greater than about 1,200 cps and even greater than about 2,000 cps (for example gels) are also within the scope of the invention provided that the compositions can be expelled through an 18 to 24 gauge needle.

In one embodiment, comprising a pharmaceutically acceptable organic solvent, the pharmaceutical composition is injectable and does not form a precipitate when injected into water.

In one embodiment, comprising a pharmaceutically acceptable organic solvent, the pharmaceutical composition is injectable and forms a precipitate when injected into water. Without wishing to be bound by theory, it is believed, for pharmaceutical compositions that comprise a protonated aptamer and an amino acid ester or amide, that the α-amino group of the amino acid ester or amino acid amide is protonated by the aptamer to form a salt, such as illustrated above, which is soluble in the pharmaceutically acceptable organic solvent but insoluble in water. Similarly, when the pharmaceutical composition comprises (i) an aptamer; (ii) a divalent metal cation; and (iii) optionally a carboxylate, a phospholipid, a phosphatidyl choline, or a sphingomyelin, it is believed that the components of the composition form a salt, such as illustrated above, which is soluble in the pharmaceutically acceptable organic solvent but insoluble in water. Accordingly, when the pharmaceutical compositions are injected into an animal, at least a portion of the pharmaceutical composition precipitates at the injection site to provide a drug depot. Without wishing to be bound by theory, it is believed that when the pharmaceutically compositions are injected into an animal, the pharmaceutically acceptable organic solvent diffuses away from the injection site and aqueous bodily fluids diffuse towards the injection site, resulting in an increase in concentration of water at the injection site, that causes at least a portion of the composition to precipitate and form a drug depot. The precipitate can take the form of a solid, a crystal, a gummy mass, or a gel. The precipitate, however, provides a depot of the aptamer at the injection site that releases the aptamer over time. The components of the pharmaceutical composition, i.e., the amino acid ester or amino acid amide, the pharmaceutically acceptable organic solvent, and any other components are biocompatible and non-toxic and, over time, are simply absorbed and/or metabolized by the body.

In one embodiment, comprising a pharmaceutically acceptable organic solvent, the pharmaceutical composition is injectable and forms liposomal or micellar structures when injected into water (typically about 500 µL are injected into about 4 mL of water). The formation of liposomal or micellar structures are most often formed when the pharmaceutical composition includes a phospholipid. Without wishing to be bound by theory, it is believed that the aptamer in the form of a salt, which can be a salt formed with an amino acid ester or amide or can be a salt with a divalent metal cation and optionally a carboxylate, a phospholipid, a phosphatidyl choline, or a sphingomyelin, that is trapped within the liposomal or micellar structure. Without wishing to be bound by theory, it is believed that when these pharmaceutically compositions are injected into an animal, the liposomal or micellar structures release the aptamer over time.

In one embodiment, the pharmaceutical composition further comprising a pharmaceutically acceptable organic solvent is a suspension of solid particles in the pharmaceutically acceptable organic solvent. Without wishing to be bound by theory, it is believed that the solid particles comprise a salt formed between the amino acid ester or amino acid amide and the protonated aptamer wherein the acidic phosphate groups of the aptamer protonates the amino group of the amino acid ester or amino acid amide, such as illustrated above, or comprises a salt formed between the aptamer; divalent metal cation; and optional carboxylate, phospholipid, phosphatidyl choline, or sphingomyelin, as illustrated above. Pharmaceutical compositions that are suspensions can also form drug depots when injected into an animal.

By varying the lipophilicity and/or molecular weight of the amino acid ester or amino acid amide it is possible to vary the properties of pharmaceutical compositions that include these components and further comprise an organic solvent. The lipophilicity and/or molecular weight of the amino acid ester or amino acid amide can be varied by varying the amino acid and/or the alcohol (or amine) used to form the amino acid ester (or amino acid amide). For example, the lipophilicity and/or molecular weight of the amino acid ester can be varied by varying the $R_1$ hydrocarbon group of the amino acid ester. Typically, increasing the molecular weight of $R_1$ increase the lipophilicity of the amino acid ester. Similarly, the lipophilicity and/or molecular weight of the amino acid amide can be varied by varying the $R_3$ or $R_4$ groups of the amino acid amide.

For example, by varying the lipophilicity and/or molecular weight of the amino acid ester or amino acid amide it is possible to vary the solubility of the aptamer in water, to vary the solubility of the aptamer in the organic solvent, vary the viscosity of the pharmaceutical composition comprising a solvent, and vary the ease at which the pharmaceutical composition can be drawn into a 20 gauge needle and then expelled from the 20 gauge needle.

Furthermore, by varying the lipophilicity and/or molecular weight of the amino acid ester or amino acid amide (i.e., by varying $R_1$ of the amino acid ester or $R_3$ and $R_4$ of the amino acid amide) it is possible to control whether the pharmaceutical composition that further comprises an organic solvent will form a precipitate when injected into water. Although different aptamers exhibit different solubility and behavior, generally the higher the molecular weight of the amino acid ester or amino acid amide, the more likely it is that the salt of the protonated aptamer and the amino acid ester of the amide will form a precipitate when injected into water. Typically, when $R_1$ of the amino acid ester is a hydrocarbon of about $C_{16}$ or higher the pharmaceutical composition will form a precipitate when injected into water and when $R_1$ of the amino acid ester is a hydrocarbon of about $C_{12}$ or less the pharmaceutical composition will not form a precipitate when injected into water. Indeed, with amino acid esters wherein $R_1$ is a hydrocarbon of about $C_{12}$ or less, the salt of the protonated aptamer and the amino acid ester is, in many cases, soluble in water. Similarly, with amino acid amides, if the combined number of carbons in $R_3$ and $R_4$ is 16 or more the pharmaceutical composition will typically form a precipitate when injected into water and if the combined number of carbons in $R_3$ and $R_4$ is 12 or less the pharmaceutical composition will not form a precipitate when injected into water. Whether or not a pharmaceutical composition that further comprises a pharmaceutically acceptable organic solvent will form a precipitate when injected into water can readily be determined by injecting about 0.05 mL of the pharmaceutical composition into about 4 mL of water at about 98° F. and determining how much material is retained on a 0.22 µm filter after the composition is mixed with water and filtered. Typically, a formulation or composition is considered to be injectable when no more than 10% of the formulation is retained on the filter. In one embodiment, no more than 5% of the formulation is retained on the filter. In one embodiment, no more than 2% of the formulation is retained on the filter. In one embodiment, no more than 1% of the formulation is retained on the filter.

Similarly, in pharmaceutical compositions that comprise a protonated aptamer and a diester or diamide of aspartic or glutamic acid, it is possible to vary the properties of pharmaceutical compositions by varying the amount and/or lipophilicity and/or molecular weight of the diester or diamide of aspartic or glutamic acid. Similarly, in pharmaceutical compositions that comprise an aptamer; a divalent metal cation; and a carboxylate, a phospholipid, a phosphatidyl choline, or a sphingomyelin, it is possible to vary the properties of pharmaceutical compositions by varying the amount and/or lipophilicity and/or molecular weight of the carboxylate, phospholipid, phosphatidyl choline, or sphingomyelin.

Further, when the pharmaceutical compositions that further comprises an organic solvent form a depot when administered to an animal, it is also possible to vary the rate at which the aptamer is released from the drug depot by varying the lipophilicity and/or molecular weight of the amino acid ester or amino acid amide. Generally, the more lipophilic the amino acid ester or amino acid amide, the more slowly the aptamer is released from the depot. Similarly, when the pharmaceutical compositions that further comprises an organic solvent and also further comprise a carboxylate, phospholipid, phosphatidyl choline, sphingomyelin, or a diester or diamide of aspartic or glutamic acid and form a depot when administered to an animal, it is possible to vary the rate at which the aptamer is released from the drug depot by varying the amount and/or lipophilicity and/or molecular weight of the carboxylate, phospholipid, phosphatidyl choline, sphingomyelin, or the diester or diamide of aspartic or glutamic acid.

Release rates from a precipitate can be measured injecting about 50 µL of the pharmaceutical composition into about 4 mL of deionized water in a centrifuge tube. The time that the pharmaceutical composition is injected into the water is recorded as T=0. After a specified amount of time, T, the sample is cooled to about −9° C. and spun on a centrifuge at about 13,000 rpm for about 20 min. The resulting supernatant is then analyzed by HPLC to determine the amount of aptamer present in the aqueous solution. The amount of aptamer in the pellet resulting from the centrifugation can also be determined by collecting the pellet, dissolving the pellet in about 10 µL of methanol, and analyzing the methanol solution by HPLC to determine the amount of aptamer in the precipitate. The amount of aptamer in the aqueous solution and the amount of aptamer in the precipitate are determined by comparing the peak area for the HPLC peak corresponding to the aptamer against a standard curve of aptamer peak area against concentration of aptamer. Suitable HPLC conditions can be readily determined by one of ordinary skill in the art.

8.6 Methods of Preparing the Aptamer Containing Pharmaceutical Compositions

The pharmaceutical compositions can be prepared by dissolving an inorganic salt of the aptamer, typically a potassium or sodium salt, in a solvent in which it is soluble, for example methanol or water, and adjusting the pH of the resulting solution to a value of between about 2 and 3 with an organic acid, such as formic acid, as depicted below:

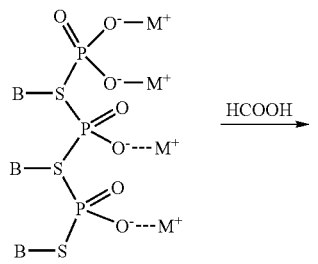

wherein S and B are defined above and M+ is a metal ion, to provide a solution of the protonated aptamer.

The resulting solution of protonated aptamer is then dialyzed against water to remove excess formic acid and formate salts and if, for example, the neutralization is conducted in a methanol solvent, to replace the methanol with water. The water can then be removed from the aqueous solution of the protonated aptamer by lyophilization to provide the protonated aptamer or, alternatively, the aqueous solution of the protonated aptamer can be dialyzed against methanol to replace the water with methanol and then simply removing the methanol under reduced pressure to provide the protonated aptamer.

A solution of the protonated aptamer can also be prepared using a cation exchange resin. Any cationion exchange resin known to one skilled in the art can be used, for example, a Strata® SCX cation exchange resin (commercially available from Phenomenex of Torrance, Calif.) or a DOWEX® cation exchange resin, such as DOWEX® 50 (commercially available from Dow Chemical Company of Midland, Mich.) can be used. Typically, a column containing the cation exchange resin is first washed with an acidic solution to protonate the resin and then a solution of the inorganic salt of the aptamer, typically a potassium or sodium salt, in a solvent, for example methanol or water, is passed through the resin to provide, as the eluant, a solution of the protonated aptamer.

To prepare the pharmaceutical compositions comprising a protonated aptamer and an a pharmaceutically acceptable organic base (using an amino acid ester or amide as a representative pharmaceutically acceptable organic base), the protonated aptamer is dissolved in a solvent, such as methanol, typically with stirring, and to the resulting solution is then added the amino acid ester or amide, as depicted below:

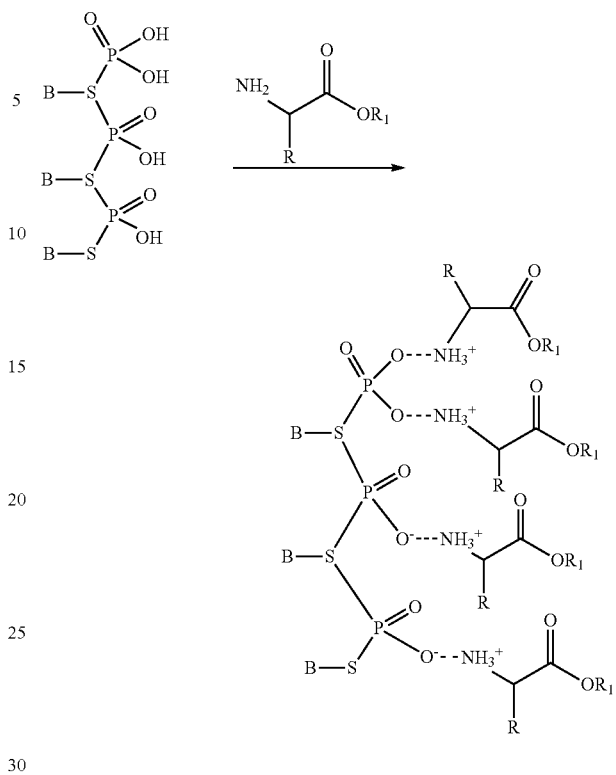

wherein S, B, R, and R$_1$ are defined above.

Any other components of the pharmaceutical composition, such as a carboxylic acid, phospholipid, phosphatidyl choline, sphingomyelin, or diester or diamide of aspartic or glutamic acid are then added to the resulting solution.

Typically, sufficient amino acid ester or amide, and any other components, are added to provide a solution having a pH value ranging from about 5 to 9. In one embodiment, sufficient amino acid ester or amide, and any other components, are added to provide a solution having a pH value ranging from about 6 to 8. In one embodiment, sufficient amino acid ester or amide, and any other components, are added to provide a solution having a pH value of about 7. The pH can be readily measured by removing a few microliters of the solution and applying it to a wet pH test strip (such as commercially available from Sigma-Aldrich of Milwaukee, Wis.) that indicates the pH of the solution by the color of the test strip after the solution is applied. The solvent is then removed under reduced pressure to provide the pharmaceutical composition comprising the amino acid ester or amino acid amide and the aptamer. The resulting composition can then be dissolved in a pharmaceutically acceptable organic solvent to provide the pharmaceutical composition comprising the amino acid ester or amino acid amide, the protonated aptamer, and a pharmaceutically acceptable organic solvent. Alternatively, the pharmaceutical compositions comprising a protonated aptamer, an amino acid ester or amide, and any other components, and a pharmaceutically acceptable organic solvent can be prepared by dissolving the protonated aptamer in the pharmaceutically acceptable solvent and adding the amino acid ester or amide and any other components to the resulting solution, preferably with stirring, to provide the pharmaceutical composition.

To prepare the pharmaceutical compositions comprising an aptamer; a divalent metal cation; and a carboxylate, a phospholipid, a phosphatidyl choline, or a sphingomyelin, the protonated aptamer is dissolved in a solvent, such as methanol, and to the resulting solution is added a metal salt, such as a metal acetate, or a metal hydroxide, preferably with stirring. To the resulting solution is then added the carboxylic acid, phospholipid, phosphatidyl choline, or sphingomyelin, preferably with stirring. The solvent is then removed under reduced pressure to provide the pharmaceutical composition comprising the aptamer; a divalent metal cation; and a carboxylate, a phospholipid, a phosphatidyl choline, or a sphingomyelin. The resulting composition can then be dissolved in a pharmaceutically acceptable organic solvent to provide the pharmaceutical composition comprising the aptamer; a divalent metal cation; and a carboxylate, a phospholipid, a phosphatidyl choline, or a sphingomyelin; and a pharmaceutically acceptable organic solvent. Alternatively, the pharmaceutical compositions comprising an aptamer; a divalent metal cation; and a carboxylate, a phospholipid, a phosphatidyl choline, or a sphingomyelin; and a pharmaceutically acceptable organic solvent can be prepared by dissolving the protonated aptamer in the pharmaceutically acceptable solvent; adding a metal salt, such as a metal acetate, or a metal hydroxide to the resulting solution, preferably with stirring; and then adding the carboxylic acid, phospholipid, phosphatidyl choline, or sphingomyelin, preferably with stirring, to provide the pharmaceutical composition.

To prepare the pharmaceutical compositions comprising a protonated aptamer and polylysine, a polylysine solution (such as a methanol solution) is slowly added to a solution (such as a methanol solution) of the protonated aptamer, preferably with stirring, and the pH of the resulting solution monitored to provide a solution having the desired pH value. The methanol is then removed under reduced pressure to provide the pharmaceutical composition comprising a protonated aptamer and polylysine.

The polylysine is obtained from commercially available polylysine hydrobromide (commercially available from Sigma-Aldrich, St. Louis, Mo.) by simply neutralizing a solution (such as a methanol or water solution) of the polylysine hydrobromide with ammonium hydroxide to provide a solution having a pH value ranging from about 10 to 12. The resulting solution of polylysine is then dialyzed against water to remove excess ammonium bromide and ammonium hydroxide and if, for example, the neutralization is conducted in a methanol solvent, to replace the methanol with water. The water can then be removed from the aqueous solution of the polylysine by lyophilization to provide the polylysine or, alternatively, the aqueous solution of the polylysine can be dialyzed against methanol to replace the water with methanol and then the methanol simply removed under reduced pressure to provide the polylysine.

8.7 Methods of Treating a Condition in an Animal

The pharmaceutical compositions of the invention are useful in human medicine and veterinary medicine. Accordingly, the invention further relates to a method of treating or preventing a condition in an animal comprising administering to the animal an effective amount of the pharmaceutical composition of the invention.

In one embodiment, the invention relates to methods of treating a condition in an animal comprising administering to an animal in need thereof an effective amount of a pharmaceutical composition of the invention.

In one embodiment, the invention relates to methods of preventing a condition in an animal comprising administering to an animal in need thereof an effective amount of a pharmaceutical composition of the invention.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical. The mode of administration is left to the discretion of the practitioner. In most instances, administration will result in the release of the aptamer into the bloodstream.

In one embodiment, the method of treating or preventing a condition in an animal comprises administering to the animal in need thereof an effective amount of an aptamer by parenterally administering the pharmaceutical composition of the invention. In one embodiment, the pharmaceutical compositions are administered by infusion or bolus injection. In one embodiment, the pharmaceutical composition is administered subcutaneously.

In one embodiment, the method of treating or preventing a condition in an animal comprises administering to the animal in need thereof an effective amount of an aptamer by orally administering the pharmaceutical composition of the invention. In one embodiment, the composition is in the form of a capsule or tablet.

The pharmaceutical compositions can also be administered by any other convenient route, for example, topically, by absorption through epithelial or mucocutaneous linings (e.g., oral, rectal, and intestinal mucosa, etc.).

The pharmaceutical compositions can be administered systemically or locally.

The pharmaceutical compositions can be administered together with another biologically active agent.

In one embodiment, the animal is a mammal.

In one embodiment the animal is a human.

In one embodiment, the animal is a non-human animal.

In one embodiment, the animal is a canine, a feline, an equine, a bovine, an ovine, or a porcine.

The effective amount administered to the animal depends on a variety of factors including, but not limited to the type of animal being treated, the condition being treated, the severity of the condition, and the specific aptamer being administered. One of ordinary skill in the art will readily know what is an effective amount of the pharmaceutical composition to treat a condition in an animal.

In one embodiment, the aptamer is a anti-Vascular Endothelial Growth Factor (VEGF) aptamer. In one embodiment, the aptamer is a anti-Vascular Endothelial Growth Factor (VEGF) aptamer and the disorder is an ocular disorder. Representative ocular disorders include, but are not limited to, age-related macular degeneration, optic disc neovascularization, iris neovascularization, retinal neovascularization, choroidal neovascularization, corneal neovascularization, vitreal neovascularization, glaucoma, pannus, pterygium, macular edema, vascular retinopathy, retinal degeneration, uveitis, inflammatory diseases of the retina, or proliferative vitreoretinopathy. Virtually any method of delivering a medication to the eye may be used for the delivery of the pharmaceutical compositions of the invention. In one embodiment, the pharmaceutical composition is administered intravitreally, for example, via intravitreal injection. In one embodiment, the pharmaceutical composition is administered transclerally.

In one embodiment, the aptamer is an aptamer that inhibits angiogenesis.

In one embodiment, the aptamer is an aptamer that inhibits angiogenesis and the disease being treated is cancer. In one embodiment, the aptamer is an aptamer that inhibits angiogenesis and the disease being treated is a solid tumor.

The following examples are set forth to assist in understanding the invention and should not be construed as specifically limiting the invention described and claimed herein.

Such variations of the invention, including the substitution of all equivalents now known or later developed, which would be within the purview of those skilled in the art, and changes in formulation or minor changes in experimental design, are to be considered to fall within the scope of the invention incorporated herein.

9 EXAMPLES

Example 1

Preparation of Amino Acid Esters

Tryptophane butanoate: 1 g of tryptophane butanoate hydrochloride salt (commercially available from Sigma-Aldrich, St. Louis, Mo.) was suspended in 25 mL of dichloromethane and 600 μl of triethylamine was added to the suspension with stirring. Stirring was continued for 15 min and the resulting solution was transferred to a separatory funnel. The organic solution was washed twice with 25 mL of water followed by 25 mL of saturated aqueous sodium bicarbonate. The organic layer was then dried over anhydrous sodium sulfate and concentrated under reduced pressure to provide tryptophane butanoate. The structure was confirmed using mass spectroscopy.

Tryptophane octanoate: 4 g of tryptophane butanoate hydrochloride salt (commercially available from Sigma-Aldrich, St. Louis, Mo. (www.sima-aldrich.com)) was suspended in 100 mL of dichloromethane and 3 ml of triethylamine was added to the suspension with stirring. Stirring was continued for 15 min and the resulting solution was transferred to a separatory funnel. The organic solution was washed twice with 25 mL of water followed by 25 mL of saturated aqueous sodium bicarbonate. The organic layer was then dried over anhydrous sodium sulfate and concentrated under reduced pressure to provide tryptophane octanoate. The structure was confirmed using mass spectroscopy.

Tyrosine butanoate: 18.19 g of tyrosine was suspended in a solution of 9.8 g of concentrated sulfuric acid, 40 mL water, 40 mL of butanol, and 200 mL of toluene in a 500 mL round bottom flask equipped with a condenser and a Dean-Stark apparatus. The resulting solution was heated at reflux temperature until no more water could be distilled. The resulting solution was cooled in an ice bath, which caused the solution to separate into two phases. The upper phase was discarded and the lower phase, an oily syrup, was retained. The syrup was mixed with sufficient 5% aqueous sodium bicarbonate solution to neutralize acidic impurities to provide a solid that was collected by filtration and washed with cold water. The resulting solid was re-crystallized in ethyl acetate.

Isoleucine butyrate: 26.23 g of isoleucine was dissolved in a solution of 20 g of concentrated sulfuric acid, 20 mL water, 40 mL of butanol, and 200 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities, washed with saturated brine, and dried over anhydrous sodium sulfate. The solvent was removed under reduced pressure and the resulting liquid distilled under vacuum to provide isoleucine butyrate as a colorless liquid.

Phenylalanine butyrate: 16.52 g of isoleucine was dissolved in a solution of 10 g of concentrated sulfuric acid, 20 mL water, 20 mL of butanol, and 200 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities, washed with saturated brine, and dried over anhydrous sodium sulfate. The solvent was removed under reduced pressure and the resulting liquid distilled under vacuum to provide phenylalanine butyrate.

Phenylalanine octanoate: 16.52 g of phenylalanine was dissolved in a solution of 10 g of concentrated sulfuric acid, 20 mL water, 20 mL of octanol, and 120 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities, washed with saturated brine, and dried over anhydrous sodium sulfate. The solvent was then removed under reduced pressure to provide phenylalanine octanoate as a white solid that was purified using a silica gel column eluted with a 1:9 methanol:dichloromethane mixture.

Phenylalanine dodecanoate: 16.52 g of phenylalanine was dissolved in a solution of 10 g of concentrated sulfuric acid, 20 mL water, 20 mL of dodecanol, and 120 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities, washed with saturated brine, and dried over anhydrous sodium sulfate. The solvent was then removed under reduced pressure to provide phenylalanine dodecanoate as a solid that was purified using a silica gel column eluted with a 1:9 methanol:dichloromethane mixture.

Tyrosine octanoate: 9.06 g of tyrosine was dissolved in a solution of 10 g of concentrated sulfuric acid, 20 mL water, 10 mL of octanol, and 200 mL of toluene in a 500 mL round bottom flask equipped with a condenser and a Dean-Stark apparatus. The resulting solution was heated at reflux temperature until no more water could be distilled. The resulting solution was then cooled to room temperature and washed with saturated aqueous sodium bicarbonate to neutralize acidic impurities to provide an emulsion. About 150 mL of ethyl acetate was added to the emulsion to provide two phases. The aqueous phase was discarded and the organic phase washed with saturated Brine and dried over anhydrous sodium sulfate. The solvent was the removed under reduced pressure to provide tyrosine octanoate as a white solid that was purified using a silica gel column eluted with a 1:9 methanol:dichloromethane mixture.

Isoleucine octanoate: 13.1 g of isoleucine was dissolved in a solution of 10 g of concentrated sulfuric acid, 20 mL water, 20 mL of octanol, and 200 mL of toluene in a 500 mL round bottom flask equipped with a condenser and a Dean-Stark apparatus placed in an oil bath. The resulting solution was heated at reflux temperature until no more water could be distilled. The resulting solution was then cooled to room temperature, diluted with 120 mL of ethyl acetate and the organic layer washed with saturated aqueous sodium bicarbonate to neutralize acidic impurities, washed with saturated Brine, and dried over anhydrous sodium sulfate. The solvent was removed under reduced pressure and the resulting liquid distilled to provide isoleucine octanoate as a colorless liquid.

Proline butanoate: 34.5 g of proline was suspended in a solution of 35 g of concentrated sulfuric acid, 40 mL water, 120 mL of butanol, and 200 mL of toluene in a 500 mL round bottom flask equipped with a condenser and a Dean-Stark apparatus. The resulting solution was heated at reflux temperature until no more water could be distilled. The resulting solution was then cooled to room temperature, washed with saturated aqueous sodium bicarbonate to neutralize acidic impurities, washed with saturated Brine, and dried over anhydrous sodium sulfate. The solvent was removed under reduced pressure and the resulting liquid distilled to provide proline butanoate as a colorless liquid.

Lysine hexadecanoate: BOC protected lysine (6.25 g, 0.018 mole) was dissolved in about 40 mL of tetrahydrofuran under a nitrogen atmosphere. The solution was cooled to about 0° C. using an ice-water bath and carbonyl diimidazole (2.93 g, 0.018 mole) was added to the cooled solution. The reaction mixture was then allowed to stir for about 5 min. at about 5° C. and then for about 30 min. at room temperature. To the resulting solution was then added by dropwise addition a solution of hexadecanol (4.38 g, 0.018 mole) in about 10 mL of tetrahydrofuran. The resulting solution was then warmed to about 45° C. and allowed to stir for about 12 h. After stirring, the solvent was evaporated under reduced pressure; the resulting residue dissolved in ethyl acetate; the ethyl acetate washed with 0.1 N hydrochloric acid (3 times), saturated aqueous sodium hydrogen carbonate (3 times), and brine (3 times); and the organic phase dried ($Na_2SO_4$). The ethyl acetate was then removed under reduced pressure to provide crude BOC protected lysine hexadecanoate that was purified using silica gel column chromatography eluted with 0 to 20 percent ethyl acetate in hexane. The solvent was then evaporated under reduced pressure to provide purified BOC protected lysine hexadecanoate. Trifluoroacetic acid (20 mL) was added to the purified BOC protected lysine hexadecanoate and the resulting reaction mixture stirred for about 5 h. Excess trifluoroacetic acid was removed under reduced pressure. The resulting residue was then dissolved in methanol and passed through a Dowex 550A(OH) resin (50 g) (commercially available from Dow Chemical Company of Midland Mich.) and the solvent removed under reduced pressure to provide lysine hexadecanoate that was dried under vacuum to provide dried lysine hexadecanoate (3.6 g).

Example 2

Pharmaceutical Composition of the Invention

A pharmaceutical compositions containing pegylated ARC259 was prepared by adding 108 mg of protonated pegylated ARC259 to 800 μL of N-methyl-2-pyrrolidone and sonicating the resulting mixture for about 25 min. to provide a clear thick solution. To the clear thick solution was then added 120 μL of a solution of isoleucine butyrate in N-methyl-2-pyrrolidone (about 71.5 mg/mL) and the resulting clear solution made up to a volume of 1 mL with N-methyl-2-pyrrolidone to provide the pharmaceutical composition.

50 μL of the pharmaceutical composition was then injected in 4 mL of water. No precipitate was observed to form when the pharmaceutical composition was injected into the water.

Example 3

Pharmaceutical Composition of the Invention

A pharmaceutical compositions containing pegylated ARC259 was prepared by adding 108 mg of protonated pegylated ARC259 to 800 μL of N-methyl-2-pyrrolidone and allowing the resulting mixture to be shaken for about 14 h. using an automatic shaker to provide a clear thick solution. To the clear thick solution was then added 120 μL of a solution of isoleucine butyrate in N-methyl-2-pyrrolidone (about 71.5 mg/mL) and the resulting clear solution made up to a volume of 1 mL with N-methyl-2-pyrrolidone to provide the pharmaceutical composition.

50 μL of the pharmaceutical composition was then injected in 4 mL of water. No precipitate was observed to form when the pharmaceutical composition was injected into the water.

Example 4

Pharmaceutical Composition of the Invention

A pharmaceutical compositions containing pegylated ARC259 was prepared by adding 108 mg of protonated pegylated ARC259 to 800 μL of glycerol formal and sonicating the resulting mixture for about 25 min. to provide a clear thick solution. To the clear thick solution was then added 120 μL of a solution of isoleucine butyrate in glycerol formal (about 71.5 mg/mL) and the resulting clear solution made up to a volume of 1 mL with glycerol formal to provide the pharmaceutical composition.

50 μL of the pharmaceutical composition was then injected in 4 mL of water. No precipitate was observed to form when the pharmaceutical composition was injected into the water.

Example 5

Viscosity of Pharmaceutical Compositions Containing an Aptamer and Amino Acid Ester in an Organic Solvent as a Function of Ester Chain Length Pharmaceutical compositions containing pegylated ARC259 at a concentration of about 10% (w/v) and 1 equivalent of isoleucine ethanoate, isoleucine butanoate, isoleucine hexanoate, isoleucine octanoate, isoleucine decanoate, isoleucine dodecanoate, or isoleucine hexadecanoate per acidic groups on the aptamer dissolved in N-methyl-2-pyrrolidone were prepared. The pharmaceutical compositions were prepared by adding 75 mg of protonated aptamer to 0.7 mL of N-methyl-2-pyrrolidone and then adding an appropriate amount of the isoleucine ester as indicated below:

| | |
|---|---|
| isoleucine ethanoate | 6.3 mg (6.8 μL) |
| isoleucine butanoate | 7.4 mg (8.46 μL) |
| isoleucine hexanoate | 8.4 mg (9.6 μL) |
| isoleucine octanoate | 9.6 mg (11.3 μL) |
| isoleucine decanoate | 10.6 mg (12.7 μL) |
| isoleucine dodecanoate | 11.7 mg (14.5 μL) |
| isoleucine hexadecanoate | 13.9 mg (17.8 μL) |

The volume of the solution was then made up to a volume of 0.75 mL with N-methyl-2-pyrrolidone, if necessary, to provide a clear solution.

The viscosity of the resulting pharmaceutical compositions was then determined using a Brookfield DV-II-PRO viscometer (commercially available from Brookfield of Marlboro, Mass.) with a cone and plate sampler, a CPE-40 spindle, a sample size of 0.5 mL, a speed of 3 rpm, and a temperature controlled to be 25° C.

FIG. 1 shows a graphical representation of the viscosity of the pharmaceutical composition v. number of carbons in the alcohol group of the isoleucine ester. The results show that, in general, increasing the number of carbons in the alcohol group of the ester decreases the viscosity of the pharmaceutical composition up to 8 carbons in the alcohol group of the ester. The $C_{12}$ ester, however, has a viscosity that is less than the $C_{16}$ ester.

Example 6

Viscosity of Pharmaceutical Compositions Containing an Amino Acid Ester and an Aptamer in an Organic Solvent as a Function of the Equivalents of Ester Per Equivalents of Acidic Functional Groups on the Aptamer Pharmaceutical compositions containing pegylated ARC259 at a concentration of about 10% (w/v) and 1 equivalent, 2 equivalents, or 6 equivalents of isoleucine decanoate per equivalent of acidic groups on the aptamer dissolved in N-methyl-2-pyrrolidone were prepared. The compositions were prepared by adding 75 mg of protonated aptamer to 0.7 mL of N-methyl-2-pyrrolidone and then adding 1 equivalent (10.6 mg, 12.7 µL), 2 equivalents (21.2 mg, 25.4 µL), or 3 equivalents (31.8 mg, 38.1 µL) of isoleucine decanoate. The volume of the solution was then made to a volume of 0.75 mL with N-methyl-2-pyrrolidone, if necessary, to provide a clear solution.

The viscosity of the resulting compositions was then determined using the method described above.

FIG. 2 shows a graphical representation of the viscosity of the pharmaceutical composition v. equivalents of isoleucine decanoate per equivalent of acidic functional groups on the aptamer. The results show that the viscosity of the pharmaceutical composition decreases as the number of equivalents of isoleucine decanoate is increased up to about 2 equivalents of isoleucine decanoate per equivalent of acidic functional groups on the aptamer. Thereafter the viscosity appears to remain unchanged up to 6 equivalents of isoleucine decanoate per equivalent of acidic functional groups on the aptamer.

Example 7

In Vitro Depot Formation of Pharmaceutical Compositions Containing an Aptamer and an Amino Acid Ester in an Organic Solvent A. Pharmaceutical compositions containing pegylated ARC259 at a concentration of about 10% (w/v) and 4 equivalents or 6 equivalents of isoleucine decanoate, isoleucine dodecanoate, or isoleucine hexadecanoate per equivalent of acidic groups on the aptamer dissolved in N-methyl-2-pyrrolidone were prepared. The compositions were prepared by adding 75 mg of protonated aptamer to 0.7 mL of N-methyl-2-pyrrolidone and then adding an appropriate amount of the ester as indicated below:

| | |
|---|---|
| 4 equivalent of isoleucine decanoate | 42.4 mg (50.8 µL) |
| 6 equivalents of isoleucine decanoate | 63.6 mg (76.2 µL) |
| 4 equivalents of isoleucine dodecanoate | 46.8 mg (58 µL) |
| 6 equivalents of isoleucine dodecanoate | 70.2 mg (87 µL) |
| 4 equivalents of isoleucine hexadecanoate | 55.6 mg (71.2 µL) |
| 6 equivalents of isoleucine hexadecanoate | 83.4 mg (106.8 µL) |

The volume of the solution was then made to a volume of 0.75 mL with N-methyl-2-pyrrolidone, if necessary, to provide a clear solution.

50 µL of each pharmaceutical composition was then injected into 4 mL of water. In each case, a precipitate was observed to form when the pharmaceutical composition was injected into the water.

B. Pharmaceutical compositions containing pegylated ARC259 at a concentration of about 10% (w/v) and 1, 2, 4, 6, 8, or 10 equivalents of lysine hexadecanoate per equivalent of acidic groups on the aptamer dissolved in N-methyl-2-pyrrolidone were also prepared following the same procedure described above to provide a clear solution. 50 µL of each composition was then injected in 4 mL of water. In each case, a precipitate was observed to form when the pharmaceutical composition was injected into the water.

When the pharmaceutical compositions having between 1 and 4 equivalents of lysine hexadecanoate per equivalent of acidic groups on the aptamer were injected into the water, an oily precipitate formed that could be made to dissolve in the water with shaking.

When the pharmaceutical compositions having between 4 and 10 equivalents of lysine hexadecanoate per equivalent of acidic groups on the aptamer were injected into the water, a gel like precipitate formed in the water that would not dissolve with shaking. Similarly, when the pharmaceutical compositions having between 4 and 10 equivalents of lysine hexadecanoate per equivalent of acidic groups on the aptamer were injected into phosphate buffered saline (PBS) or into water containing about 0.643 µM bovine serum albumen (BSA), a gel like precipitate formed in the aqueous media that would not dissolve with shaking. The greater the number of equivalents of lysine hexadecanoate per equivalent of acidic groups on the aptamer, the longer the precipitate remained before dissolving. For example, for pharmaceutical compositions having 4 equivalents of lysine hexadecanoate per equivalent of acidic groups on the aptamer, the precipitate remained for about 2 days before dissolving. For pharmaceutical compositions having 6 equivalents and 10 equivalents of lysine hexadecanoate per equivalent of acidic groups on the aptamer, the precipitate remained for about 4 days and 6 days, respectively, before dissolving.

Example 8

Pharmaceutical Compositions Containing an Aptamer and a Lysine Ester and a Fatty Acid in an Organic Solvent A pharmaceutical composition was prepared by adding 100 mg of pegylated ARC259 and 9.6 mg of the ester formed between lysine hexadecanoate (about 1 eq. per equivalent of acidic groups on the aptamer) to 650 µL of N-methyl-2-pyrrolidone. An additional 30.4 mg of the lysine hexadecanoate was then added to the resulting solution followed by 15 mg of lauric acid. The volume of the resulting solution was then made up to 1 mL with N-methyl-2-pyrrolidone to provide a clear solution. When 50 µL of the pharmaceutical composition was injected into 4 mL of water, a precipitate was observed to form.

Example 9

Pharmaceutical Compositions Containing an Aptamer, an Isoleucine Ester, and a Phospholipid A solution was prepared by dissolving 307 mg of Phospholipon® 80 (commercially available from Phospholipid GmbH of Cologne, Germany or American Lecithin Company of Oxford, Conn.) in 5 mL of N-methyl-2-pyrrolidone to provide "solution A." 108 mg of pegylated ARC259 was then dissolved in 800 µL of solution A followed by 11.5 µL of isoleucine butyrate. The resulting mixture was then sonicated to provide a clear solution and the volume of the solution was made up to 1 mL with solution A to provide the pharmaceutical composition as a clear solution. When 50 µL of the pharmaceutical composition was injected into 4 mL of water, a gel like precipitate was observed to form. When the solution of the precipitate in water was shaken, liposomal and micellar structures were also observed which may not be retained on a 0.22 µm filter.

Similar pharmaceutical compositions can be made using other esters or amides of amino acids, other organic solvents, and/or other phospholipids.

Example 10

Pharmaceutical Compositions Containing an Aptamer, a Divalent Metal Ion, and a Phospholipid A pharmaceutical composition was prepared by dissolving 19 mg of pegylated ARC259 in 0.5 mL of N-methyl-2-pyrrolidone containing 10% (w/v) of Phospholipon® 80 (commercially available from Phospholipid GmbH of Cologne, Germany or American Lecithin Company of Oxford, Conn.). To the resulting solution was added 0.4 mL of neat N-methyl-2-pyrrolidone followed by 25 mg of zinc acetate with mixing to provide a clear solution. When 50 µL of the pharmaceutical composition was injected into 4 mL of water, a gel like precipitate was observed to form. When the solution of the precipitate in water was shaken, liposomal and micellar structures were also observed which may not be retained on a 0.22 µm filter.

Similar pharmaceutical compositions can be made using other esters or amides of amino acids, other divalent metal ions, other organic solvents, and/or other phospholipids.

Example 11

HPLC Analysis of the Pharmaceutical Compositions of the Invention and Method for Measuring Rate of Release of the Aptamer from the Pharmaceutical Compositions of the Invention The amount of aptamer released from a precipitate as a function of time can be measured by injecting about 50 µL of the pharmaceutical composition into about 4 mL of deionized water in a centrifuge tube to form the precipitate. The time that the pharmaceutical composition is injected into the water is recorded as T=0. After a specified amount of time, T, the sample, optionally cooled to about −9° C., is spun on a centrifuge at about 13,000 rpm for about 20 min. to provide a pellet and a supernatant liquid that can be easily separated by decanting the supernatant. The resulting supernatant is then analyzed by a suitable HPLC method to determine the amount of aptamer present in the aqueous solution. The amount of aptamer in the pellet can also be determined by dissolving the pellet in about 3 mL of methanol and analyzing the methanol solution by a suitable HPLC method to determine the amount of aptamer in the precipitate. The amount of aptamer in the aqueous solution and the amount of aptamer in the precipitate can be determined by comparing the peak area for the HPLC peak corresponding to the aptamer against a standard curve of aptamer peak area against concentration of aptamer. Suitable HPLC methods can be readily determined by one of ordinary skill in the art. For example for the aptamer used in the above experiments (i.e., pegylated ARC259) the following HPLC method can be used.

| | |
|---|---|
| Column: | Jupiter 5µ C4 300 A, 30 × 4.6 mm (Part # 00A-4167-EO). |
| Flow rate: | 2.0 mL/min. |

-continued

| | |
|---|---|
| Injection volume: | 20 µL |
| Detector setting: | 258 nm |
| Run Time: | 10 min. |
| Pump A: | Option 1 (Acidic mobile phase): 25 mM Ammonium Acetate-Trifluoroacetic Acid (TFA), pH 4.76 or |
| Pump A: | Option 2 (Basic mobile phase): 50 mM Triethanolamine-HCl, pH 7.8 |
| Pump B: | Methanol |
| Initial Conditions: | 0% pump B          100% pump A |

The HPLC column is eluted using the following gradient elution profile:

| Time (min) | Module | Function | Value | Duration (min) |
|---|---|---|---|---|
| 0.00 | pump | % B | 90.00 | 3.00 |
| 6.00 | pump | % B | 0.00 | 0.50 |
| 6.00 | pump | Flow Rate | 4.00 | 0.00 |
| 10.00 | Detector | | stop acquiring data | |

Under these conditions the aptamer has a retention time of about 3 min.

50 µL of the pharmaceutical composition of Example 7B containing 10 equivalents of lysine hexadecanoate was injected into 4 mL of water to provide a precipitate and the precipitate and supernatant were separated by centrifugation following the procedure described above to provide a pellet and a supernatant liquid. The pellet was dissolved in about 3 mL of methanol. The supernatant and the methanol solution of the pellet were then analyzed by HPLC using the conditions described above using the basic mobile phase.

FIG. 3 shows an HPLC chromatogram of the supernatant (lower trace) and an HPLC chromatogram of the methanol solution of the pellet (upper trace). The HPLC chromatogram shows that about 5% of the aptamer was in the supernatant and about 95% of the aptamer was in the pellet.

FIG. 4 shows HPLC analysis of the pharmaceutical composition of Example 4B containing 10 equivalents of lysine hexadecanoate. 50 µL of the pharmaceutical composition was injected into about 3 mL of methanol and the resulting methanol solution analyzed by HPLC using the HPLC parameters described above. Trace A is the HPLC chromatogram the pharmaceutical composition obtained using the basic mobile phase. Trace B is the HPLC chromatogram the pharmaceutical composition obtained using the acidic mobile phase. Trace C is the HPLC chromatogram of the aptamer dissolved in methanol using the basic mobile phase.

FIG. 4 also shows that when the pharmaceutical composition is analyzed using the acidic mobile phase a less sharp peak at a later retention time is obtained (Trace B) compared to analysis using the basic mobile phase. Without wishing to be bound by theory, it is believed that when using the acidic mobile, the aptamer and the lysine hexadecanoate remain associated resulting in the peak corresponding to the aptamer eluting later and being a less sharp peak. When using the basic mobile phase, however, the aptamer and the lysine hexadecanoate are not associated resulting in the peak corresponding to the aptamer eluting earlier as a sharper peak. FIG. 4 shows that the basic mobile phase is better for analyzing the aptamer by HPLC.

FIG. 4 also shows that the complex between the aptamer and the amino acid (in this example lysine hexadecanoate) remain associated under acidic conditions. Accordingly, this suggests that when a pharmaceutical composition of the invention is orally administered to an animal, it is likely that the complex between the aptamer and the amino acid will remain associated in the acidic environment of the stomach, which could result in extended release of the aptamer and/or better absorption of the aptamer.

Example 12

Pharmaceutical Compositions Containing an Aptamer a Lysine Ester and a Fatty Acid in an Organic Solvent, Wherein the Lysine Ester is Present in an Excess Relative to the Aptamer A pharmaceutical composition was prepared by adding 100 mg of pegylated ARC259 to 1 mL of N-methyl-2-pyrrolidone. The resulting mixture was mixed using a vortex mixer and occasionally sonicated to provide a clear viscous solution. To the clear viscous solution was added 40 mg of lysine hexadecanoate and the resulting mixture mixed using a vortex mixer to provide a clear solution. The pH of the resulting solution, determined as described above using a wet pH test strip (such as commercially available from Sigma-Aldrich of Milwaukee, Wis.), was basic. To the basic solution was added 15 mg of lauric acid and the resulting mixture mixed using a vortex mixer to provide a clear solution. The pH of the clear solution, determined as described above using a wet pH test strip was neutral, i.e., about pH 7. When 50 μL of the pharmaceutical composition was injected into 4 mL of water, a precipitate was observed to form.

Example 13

Pharmaceutical Compositions Containing an Aptamer and a Polycarboxylic Acid

A pharmaceutical composition was prepared by adding 100 mg of pegylated ARC259 to 1 mL of N-methyl-2-pyrrolidone. The resulting mixture was mixed using a vortex mixer and occasionally sonicated to provide a clear viscous solution. To the clear viscous solution was added 8 mg of polyacrylic acid (20,000 molecular weight, commercially available from Sigma-Aldrich of Milwaukee, Wis.) and the resulting mixture mixed using a vortex mixer to provide a clear solution. The pH of the resulting solution, determined as described above using a wet pH test strip (such as commercially available from Sigma-Aldrich of Milwaukee, Wis.), was slightly basic. To the slightly basic solution was added a small amount of the polyacrylic acid, the mixture mixed well using a vortex mixer, and the pH checked again. Additional small amounts of the of polyacrylic acid were added with mixing and the pH of the resulting solution checked until the pH of the resulting solution was about pH 7. When 50 μL of the pharmaceutical composition was injected into 4 mL of water, a precipitate was observed to form.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosure of which are incorporated.

What is claimed is:
1. A pharmaceutical compositions comprising:
   (i) an aptamer;
   (ii) a divalent metal cation;
   (iii) a pharmaceutically acceptable organic solvent; and
   (iv) one or more of a carboxylate, a phospholipid, a phosphatidyl choline, or a sphingomyelin,
   wherein the combined molar ratio of the anionic groups on the aptamer and the anionic groups on the carboxylate, phospholipid, phosphatidyl choline, or sphingomyelin to the divalent metal cation ranges from about 15:1 to 1:15, and
   wherein the pharmaceutical composition is injectable and forms a precipitate when injected into water.
2. The pharmaceutical composition of claim 1, wherein the pharmaceutical composition is a solution and the concentration of the aptamer in the pharmaceutically acceptable organic solvent is at least 2 percent by weight of the pharmaceutical composition or about 2% by weight of the composition.
3. The composition of claim 1, wherein the composition forms a depot when administered to an animal.
4. The pharmaceutical composition of claim 1, wherein the divalent metal ion is selected from the group consisting of the alkaline earth metal cations, $Zn^{+2}$, $Cu^{+2}$, and $Fe^{+2}$.
5. The pharmaceutical composition of claim 1, wherein the divalent metal ion is selected from the group consisting of $Ca^{+2}$, $Mg^{+2}$, $Zn^{+2}$, $Cu^{+2}$, and $Fe^{+2}$.
6. The pharmaceutical composition of claim 1, wherein the pharmaceutically acceptable organic solvent is selected from the group consisting of pyrrolidone, N-methyl-2-pyrrolidone, polyethylene glycol, propylene glycol, glycerol formal, isosorbid dimethyl ether, ethanol, dimethyl sulfoxide, tetraglycol, tetrahydrofurfuryl alcohol, triacetin, propylene carbonate, dimethyl acetamide, dimethyl formamide, dimethyl sulfoxide.
7. The pharmaceutical composition of claim 1, wherein the pharmaceutically acceptable organic solvent is a water soluble solvent.
8. The pharmaceutical composition of claim 1, wherein the pharmaceutically acceptable organic solvent is a water miscible organic solvent.
9. The pharmaceutical composition of claim 8, wherein the pharmaceutically acceptable organic solvent is selected from the group consisting of glycerol formal, polyethylene glycol, and propylene glycol.
10. The pharmaceutical composition of claim 1, wherein the one or more of a carboxylate, a phospholipid, a phosphatidyl choline, or a sphingomyelin is a carboxylate.
11. The composition of claim 10, wherein the composition forms a depot when administered to an animal.
12. The pharmaceutical composition of claim 10, wherein the divalent metal ion is selected from the group consisting of the alkaline earth metal cations, $Zn^{+2}$, $Cu^{+2}$, and $Fe^{+2}$.
13. The pharmaceutical composition of claim 10, wherein the divalent metal ion is selected from the group consisting of $Ca^{+2}$, $Mg^{+2}$, $Zn^{+2}$, $Cu^{+2}$, and $Fe^{+2}$.
14. The pharmaceutical composition of claim 10, wherein the pharmaceutically acceptable organic solvent is selected from the group consisting of pyrrolidone, N-methyl-2-pyrrolidone, polyethylene glycol, propylene glycol, glycerol formal, isosorbid dimethyl ether, ethanol, dimethyl sulfoxide, tetraglycol, tetrahydrofurfuryl alcohol, triacetin, propylene carbonate, dimethyl acetamide, dimethyl formamide, dimethyl sulfoxide.

15. The pharmaceutical composition of claim 10, wherein the pharmaceutically acceptable organic solvent is a water soluble solvent.

16. The pharmaceutical composition of claim 10, wherein the pharmaceutically acceptable organic solvent is a water miscible organic solvent.

17. The pharmaceutical composition of claim 16, wherein the pharmaceutically acceptable organic solvent is selected from the group consisting of glycerol formal, polyethylene glycol, and propylene glycol.

18. The pharmaceutical composition of claim 10, wherein the carboxylate is a carboxylate of a fatty acid.

19. The pharmaceutical composition of claim 10, wherein the carboxylate is a carboxylate of a polycarboxylic acid.

20. The pharmaceutical composition of claim 10, wherein the carboxylate is a carboxylate of an N-acylamino acid of formula (III):

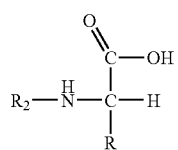

(III)

wherein:
R is an amino acid side chain; and
$R_2$ is an acyl group of formula —C(O)—$R_5$, wherein $R_5$ is a substituted $C_1$ to $C_{21}$ hydrocarbon group.

21. The pharmaceutical composition of claim 1, further comprising a pharmaceutically acceptable polymer.

22. The pharmaceutical composition of claim 21, wherein the polymer is present in an amount ranging from about 0.1 to 10 percent by weight of the composition.

23. The pharmaceutical composition of claim 1, wherein the ratio of anionic groups on the aptamer and anionic groups on the carboxylate, phospholipid, phosphatidyl choline, or sphingomyelin to the divalent metal cation ranges from about 4:1 to 1:4.

24. The pharmaceutical composition of claim 10, wherein the carboxylate is a $C_1$-$C_{16}$ carboxylate.

25. The pharmaceutical composition of claim 10, wherein the carboxylate is a $C_1$-$C_{10}$ carboxylate.

26. The pharmaceutical composition of claim 10, wherein the carboxylate is a $C_6$-$C_{22}$ carboxylate.

27. The pharmaceutical composition of claim 10, wherein the carboxylate is a $C_6$-$C_{18}$ carboxylate.

28. The pharmaceutical composition of claim 19, wherein the polycarboxylic acid is selected from the group consisting of oxalic acid, malonic acids, succinic acid, glutamic acid, adipic acid, pimelic acid, and combinations thereof.

29. The pharmaceutical composition of claim 1, wherein the composition forms liposomal or micelle structures when shaken.

* * * * *